(12) United States Patent
Bonnette et al.

(10) Patent No.: US 7,334,681 B2
(45) Date of Patent: *Feb. 26, 2008

(54) PACKAGING SYSTEM WITH OXYGEN SENSOR FOR GAS INFLATION/EVACUATION SYSTEM AND SEALING SYSTEM

(75) Inventors: Michael J. Bonnette, Minneapolis, MN (US); Eric J. Thor, Arden Hills, MN (US); Mark L. Jenson, Greenfield, MN (US)

(73) Assignee: Possis Medical, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/654,741

(22) Filed: Jan. 18, 2007

(65) Prior Publication Data

US 2007/0163910 A1    Jul. 19, 2007

Related U.S. Application Data

(63) Continuation-in-part of application No. 10/748,452, filed on Dec. 30, 2003, now Pat. No. 7,219,799, and a continuation-in-part of application No. 10/838,464, filed on May 4, 2004, now Pat. No. 7,220,243, which is a continuation-in-part of application No. 10/007,788, filed on Nov. 6, 2001, now Pat. No. 6,942,678, and a continuation-in-part of application No. 10/012,903, filed on Nov. 6, 2001, now Pat. No. 6,932,828.

(60) Provisional application No. 60/437,624, filed on Dec. 31, 2002.

(51) Int. Cl.
*B65D 85/20* (2006.01)
*A61M 25/10* (2006.01)

(52) U.S. Cl. .............. 206/459.1; 206/807; 206/571; 606/191; 436/1; 436/136

(58) Field of Classification Search ............ 206/459.1, 206/807, 204–213.1, 438, 484, 484.2; 436/1, 436/3, 135; 426/136
See application file for complete search history.

(56) References Cited

U.S. PATENT DOCUMENTS

| 4,166,807 A | * | 9/1979 | Komatsu et al. ............... 502/62 |
| 5,014,494 A | * | 5/1991 | George ........................ 53/425 |
| 5,196,245 A | * | 3/1993 | DeRudder et al. ......... 428/35.5 |
| 5,399,658 A | * | 3/1995 | Archey et al. .............. 528/198 |

(Continued)

OTHER PUBLICATIONS

Material Data Sheet for Dow Calibre 2081 polycarbonate revealing the color stability for which the material was created.*

*Primary Examiner*—Mickey Yu
*Assistant Examiner*—Jerrold Johnson
(74) *Attorney, Agent, or Firm*—Hugh D. Jaeger, Esq.

(57) ABSTRACT

A storable gas inflation/evacuation system and sealing system. The systems are removably connectible to a proximal portion of a guidewire assembly which has an occlusive balloon at a distal portion. The invention includes provision for indicating the presence of oxygen which is undesirable. The storable aspect concerns a sealable container isolating systems components from ambient atmosphere and an oxygen-sensitive material located within the sealable container. The oxygen-sensitive material is initially inactive but activated by exposure to radiation so as to visually change in response to post-radiation oxygen exposure.

16 Claims, 22 Drawing Sheets

U.S. PATENT DOCUMENTS

| | | | |
|---|---|---|---|
| 5,474,194 A | * 12/1995 | Heilman et al. | 215/230 |
| 5,583,047 A | * 12/1996 | Blinka et al. | 436/5 |
| 5,881,534 A | * 3/1999 | Ahlqvist et al. | 53/403 |
| 6,161,695 A | * 12/2000 | Nicolais | 206/438 |
| 6,166,116 A | * 12/2000 | Sleeckx | 524/168 |
| 6,485,657 B1 | * 11/2002 | Funakoshi et al. | 252/478 |
| 6,494,314 B1 | * 12/2002 | Lamborne et al. | 206/0.6 |
| 6,927,063 B2 | * 8/2005 | Moreton et al. | 436/39 |
| 2004/0050740 A1 | * 3/2004 | Lewis | 206/459.1 |

* cited by examiner

T = 1 WEEK

T = 0

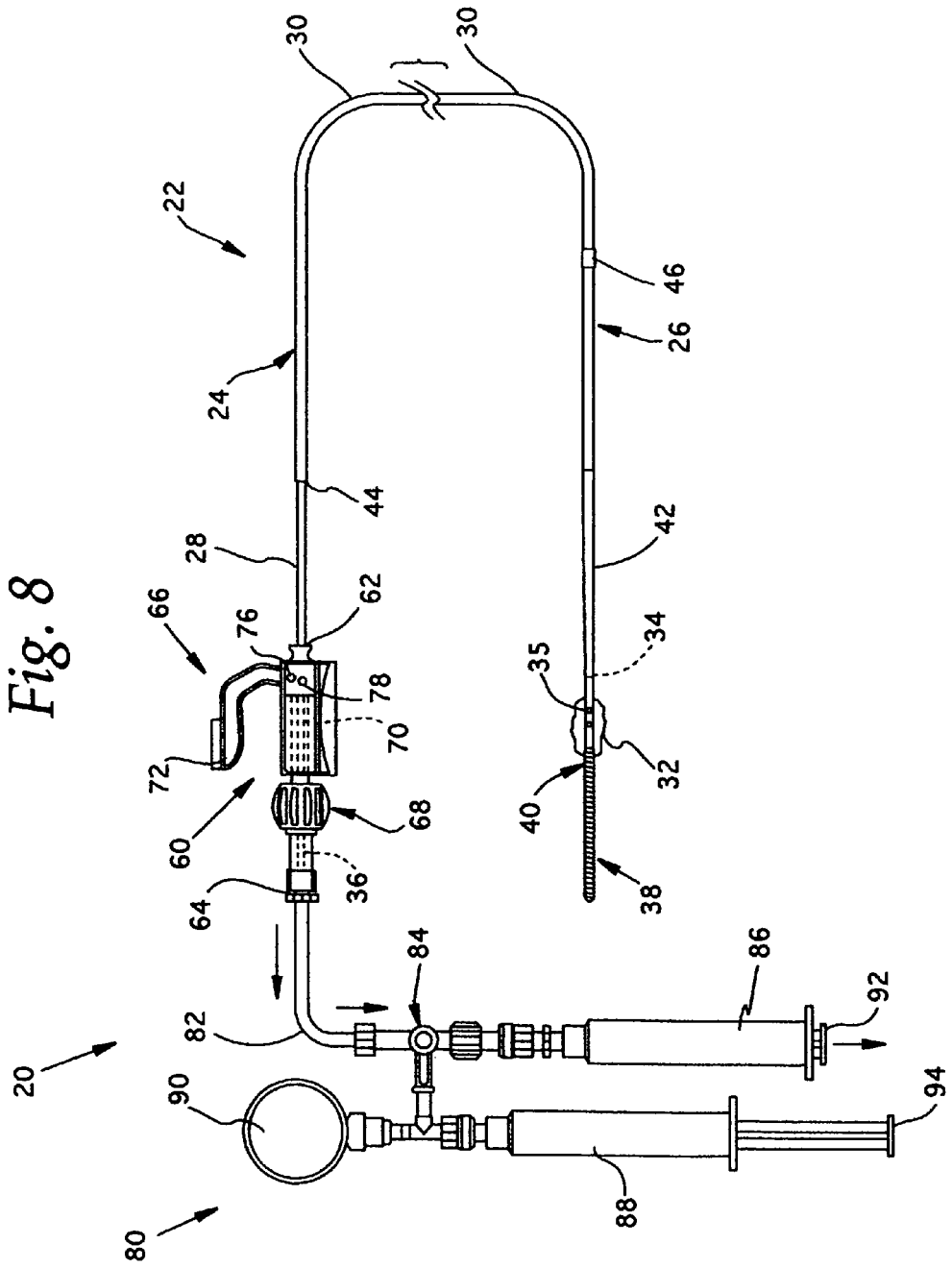

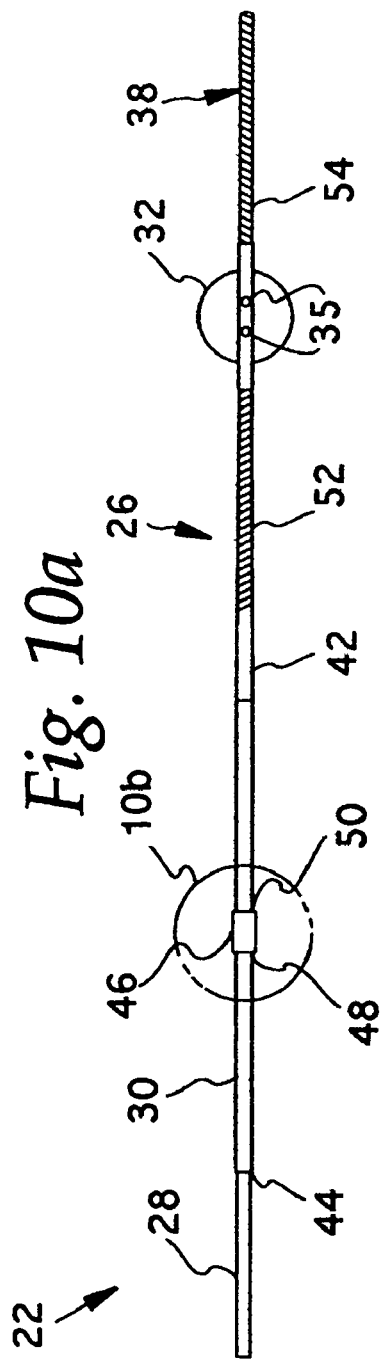
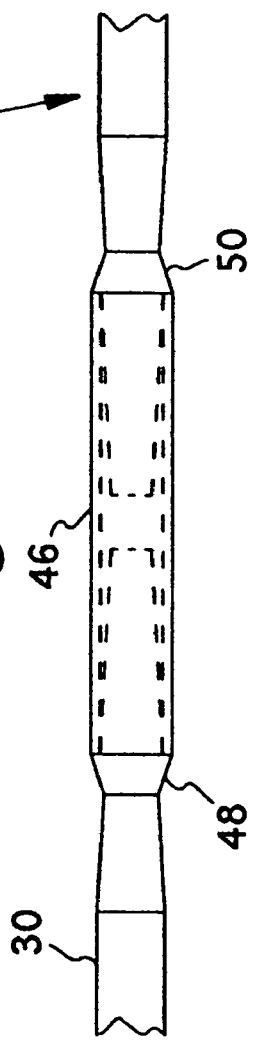

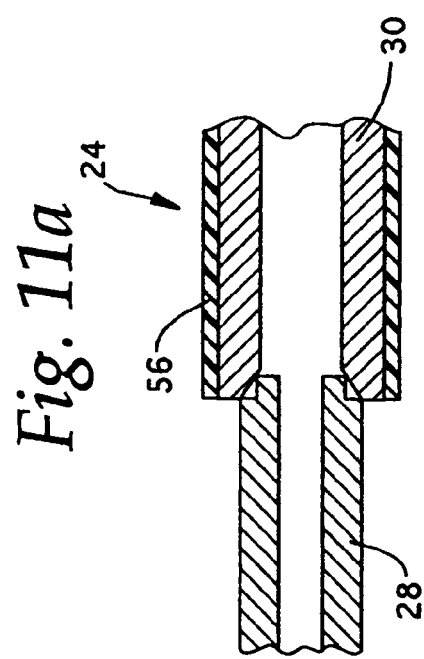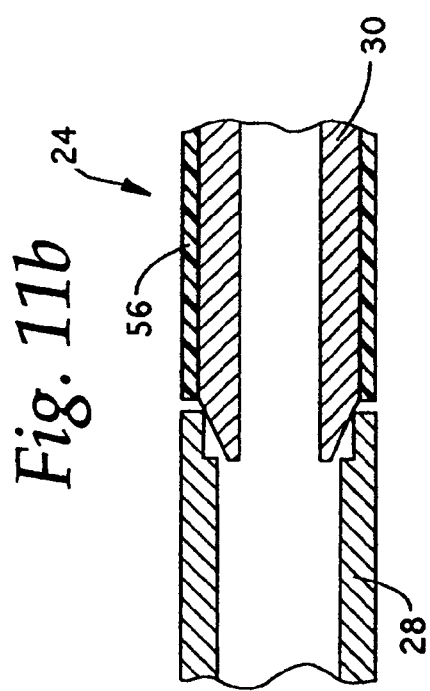

PACKAGING SYSTEM WITH OXYGEN SENSOR FOR GAS INFLATION/EVACUATION SYSTEM AND SEALING SYSTEM

CROSS REFERENCES TO RELATED APPLICATIONS

This patent application is a continuation-in-part of application Ser. No. 10/748,452 entitled "Packaging System with Oxygen Sensor" filed Dec. 30, 2003, now U.S. Pat. No. 7,219,799, which claims benefit from the earlier filed U.S. Provisional Application No. 60/437,624 entitled "Packaging System with Oxygen Sensor", filed Dec. 31, 2002, and is hereby incorporated into this application by reference as if fully set forth herein. This patent application is also a continuation-in-part of application Ser. No. 10/838,464 filed May 4, 2004, now U.S. Pat. No. 7,220,243 entitled "Gas Inflation/Evacuation System and Sealing System Incorporating a Compression Sealing Mechanism for Guidewire Assembly Having Occlusive Device", which application in turn is a continuation-in-part of application Ser. No. 10/007,788 filed Nov. 6, 2001, entitled "Gas Inflation/Evacuation System for Guidewire Having Occlusive Device", now U.S. Pat. No. 6,942,678 issued Sep. 13, 2005, and which are incorporated by reference as if fully set forth herein, and also a continuation-in-part of application Ser. No. 10/012,903 filed Nov. 6, 2001, entitled "Guidewire Occlusion System Utilizing Repeatably Inflatable Gas-Filled Occlusive Device", now U.S. Pat. No. 6,932,828 issued Aug. 23, 2005, also incorporated by reference as if fully set forth herein.

BACKGROUND OF THE INVENTION

1. Field of the Invention

The present invention relates to the field of packaging of sterile or oxygen-sensitive products, such as medical products and food products. More particularly, the present invention is directed to methods and arrangements for packaging oxygen-sensitive items, whereby a change in appearance of a material visually indicates the presence of oxygen inside the packaging. Additionally, the present invention relates generally to the field of vascular medical devices. More specifically, the present invention relates to a gas inflation/evacuation system and sealing system for selectively and repeatedly inflating an occlusive balloon and crimping an extended sealable section proximate the proximal end of a guidewire assembly during an occlusion procedure.

2. Description of the Prior Art

In certain applications, such as pharmaceutical storage or food processing, it is desirable to package the product in a controlled atmosphere or environment to ensure freshness, to promote proper chemical activity, or to prevent microbial contamination. The controlled atmosphere can be an inert gas such as nitrogen or carbon dioxide, or it could be a noble gas. In some applications, the controlled environment could be a vacuum. In those applications where a controlled atmosphere or environment is desirable, it may be beneficial to be able to determine that the desired controlled atmosphere or environment has not been compromised. The presence of oxygen in a previously evacuated sample indicates that atmospheric penetration has occurred and that the controlled atmosphere has been compromised. Thus, oxygen detection is one method for determining if a controlled atmosphere has been breached.

In the medical and food processing industries, it may be desirable to sterilize medical and food products after these products have been placed inside containers with controlled environments. The medical and food processing industries have sterilized some appropriate products with gamma radiation. Gamma radiation, which can be derived from cobalt 60, is lethal to bacteria and other microorganisms due to the effect that the radiation has on living cells. In addition, gamma radiation can be detrimental to some chemical systems and compositions. The dose or amount of radiation absorbed is typically measured in either Megarads or Kilograys, where 1 Megarad is equivalent to 10 Kilograys. In general, a 2.5 Megarad, or 25 Kilogray, dose of gamma radiation can be sufficient to kill most microorganisms.

Gamma radiation is composed of high energy photons with wavelengths generally shorter than about 0.1 nm. Gamma radiation is emitted from atomic nuclei during radioactive decay and generally follows the ejection of beta rays from the nucleus. X-rays are similar to gamma rays in the sense that both are highly energetic and penetrating forms of radiation. However, gamma rays usually have shorter wavelengths than X-rays, and as a result, gamma rays are slightly higher in energy than X-rays.

As a result of the increased use of gamma radiation sterilization and packaging in controlled environments, there is a need for oxygen-sensitive materials that can be placed inside medical and food product containers which can detect the presence of oxygen after the container has been irradiated, and possibly sterilized, with gamma radiation.

Currently, there are several types of oxygen, and oxidation, sensors designed to be used in packaging applications. See, for example, U.S. Pat. No. 4,526,752 to Perlman et al., U.S. Pat. No. 5,096,813 to Krumhar et al., U.S. Pat. No. 6,399,387 to Stenhom et al., and U.S. Pat. No. 6,325,974 to Ahvenainen et al. However, none of these patents are directed toward oxygen-sensitive materials that are activated by radiation. Furthermore, the above mentioned sensors are not suitable to form component parts for other devices. With the volume of medical devices and food products being produced, it would be desirable to provide an oxygen sensor that was easily stored in oxygen-rich environments and could be activated upon exposure to gamma radiation in the absence of oxygen.

The following additional background may be of assistance in understanding the present invention. Arterial disease involves damage that happens to the arteries in the body. Diseased arteries can become plugged with thrombus, plaque, or grumous material that may ultimately lead to a condition known as ischemia. Ischemia refers to a substantial reduction or loss of blood flow to the heart muscle or any other tissue that is being supplied by the artery and can lead to permanent damage of the affected region. While arterial disease is most commonly associated with the formation of hard plaque and coronary artery disease in the heart, similar damage can happen to many other vessels in the body, such as the peripheral vessels, cerebral vessels, due to the buildup of hard plaque or softer thrombus or grumous material within the lumen of an artery or vein.

A variety of vascular medical devices and procedures have been developed to treat diseased vessels. The current standard procedures include bypass surgery (where a new blood vessel is grafted around a narrowed or blocked artery) and several different types of nonsurgical interventional vascular medical procedures, including angioplasty (where a balloon on a catheter is inflated inside a narrowed or blocked portion of an artery in an attempt to push back plaque or thrombotic material), stenting (where a metal mesh tube is expanded against a narrowed or blocked portion of an artery to hold back plaque or thrombotic material), and debulking techniques in the form of atherectomy (where some type of high speed or high power mechanism is used to dislodge hardened plaque) or thrombectomy (where some type of mechanism or infused fluid is used to dislodge grumous or thrombotic material). In each of these interventional vascular medical procedures, a very flexible guidewire is routed through the patient's vascular system to a desired treatment location and then a catheter that includes a device on the distal end appropriate for the given procedure is tracked along the guidewire to the treatment location.

Although interventional vascular procedures avoid many of the complications involved in surgery, there is a possibility of complications if some of the plaque, thrombus or other material breaks free and flows downstream in the artery or other vessel, potentially causing a stroke, a myocardial infarction (heart attack), or other tissue death. One solution to this potential complication is to use some kind of occlusive device to block or screen the blood flowing downstream of the treatment location. Examples of catheter arrangements that use a pair of balloons as occlusive devices to create an isolated space in the blood vessel are described in U.S. Pat. Nos. 4,573,966, 4,636,195, 5,059,178, 5,320,604, 5,833,644, 5,925,016, 6,022,336 and 6,176,844. Examples of catheter arrangements that use a single balloon as an occlusive device either upstream or downstream of the treatment location are described in U.S. Pat. Nos. 5,171,221, 5,195,955, 5,135,482, 5,380,284, 5,688,234, 5,713,917, 5,775,327, 5,792,179, 5,807,330, 5,833,650, 5,843,022, 6,021,340, 6,159,195 and 6,248,121. An example of a catheter arrangement that uses a mechanically-expanded occlusive device is shown in U.S. Pat. No. 6,231,588. Occlusive balloons also have been used on non-over-the-wire catheters without any guidewire internal to the catheter as described, for example, in U.S. Pat. Nos. 4,838,268 and 5,209,727.

The use of an occlusive device as part of a vascular procedure is becoming more common in debulking procedures performed on heart bypass vessels. Most heart bypass vessels are harvested and transplanted from the saphenous vein located along the inside of the patient's leg. The saphenous vein is a long, straight vein that has a capacity more than adequate to support the blood flow needs of the heart. Once transplanted, the saphenous vein is subject to a buildup of plaque or thrombotic materials in the grafted arterial lumen. Unfortunately, the standard interventional vascular treatments for debulking are only moderately successful when employed to treat saphenous vein coronary bypass grafts. The complication rate for a standard balloon angioplasty procedure in a saphenous vein coronary bypass graft is higher than in a native vessel with the complications including embolization, "no-reflow" phenomena, and procedural related myocardial infarction. Atherectomy methods including directional, rotational, and laser devices are also associated with a high degree of embolization resulting in a greater likelihood of infarction. The use of stents for saphenous vein coronary bypass grafts has produced mixed results. Stents provide for less restenosis, but they do not eliminate the risk of embolization and infarction incurred by standard balloon angioplasty.

In order to overcome the shortcomings of these standard nonsurgical interventional treatments in treating saphenous vein coronary bypass graft occlusion, embolic protection methods utilizing a protective device distal to the lesion have been developed. The protective device is typically a filter or a balloon. Use of a protective device in conjunction with an atherectomy or thrombectomy device is intended to prevent emboli from migrating beyond the protective device and to allow the embolic particles to be removed, thereby subsequently reducing the risk of myocardial infarction. When the occlusive device is a balloon, the balloon is inserted and inflated at a point distal to the treatment site or lesion site. Therapy is then performed at the treatment site and the balloon acts to block all blood flow which prevents emboli from traveling beyond the balloon. Following treatment, some form of particle removal device must be used to remove the dislodged emboli prior to balloon deflation. U.S. Pat. No. 5,843,022 uses a balloon to occlude the vessel distal to a lesion or blockage site. The occlusion is treated with a high pressure water jet, and the fluid and entrained emboli are subsequently removed via an extraction tube. U.S. Pat. No. 6,135,991 describes the use of a balloon to occlude the vessel allowing blood flow and pressure to prevent the migration of emboli proximally from the treatment device.

There are various designs that have included an occlusive balloon on the end of a guidewire. U.S. Pat. Nos. 5,520,645, 5,779,688 and 5,908,405 describe guidewires having removable occlusive balloons on a distal end. U.S. Pat. No. 4,573,470 describes a guidewire having an occlusive balloon where the guidewire is bonded inside the catheter as an integral unit. U.S. Pat. Nos. 5,059,176, 5,167,239, 5,520,645, 5,779,688 and 6,050,972 describe various guidewires with balloons at the distal end in which a valve arrangement is used to inflate and/or deflate the balloon. U.S. Pat. No. 5,908,405 describes an arrangement with a removable balloon member that can be repeatedly inserted into and withdrawn from a guidewire. U.S. Pat. No. 5,776,100 describes a guidewire with an occlusive balloon adhesively bonded to the distal end with an adapter on the proximal end to provide inflation fluid for the occlusive balloon.

Except in the case of the normal cerebral anatomy where there are redundant arteries supplying blood to the same tissue, one of the problems with using an occlusive device in the arteries is that tissue downstream of the occlusive device can be damaged due to the lack of blood flow. Consequently, an occlusive device that completely blocks the artery can only be deployed for a relatively short period of time. To overcome this disadvantage, most of the recent development in relation to occlusive devices has focused on devices that screen the blood through a filter arrangement. U.S. Pat. Nos. 5,827,324, 5,938,672, 5,997,558, 6,080,170, 6,171,328, 6,203,561 and 6,245,089 describe various examples of filter arrangements that are to be deployed on the distal end of a catheter system. While a filter arrangement is theoretically a better solution than an occlusive device, in practice such filter arrangements often become plugged, effectively turning the filter into an occlusive device. The filter arrangements also are mechanically and operationally more complicated than an occlusive balloon device in terms of deployment and extraction.

As is the case in almost all angioplasty devices or stenting catheter devices where a balloon is used to expand the blood vessel or stent, most catheter occlusive balloons, as well as most guidewire occlusive balloons, utilize a liquid fluid, such as saline or saline mixed with a radiopaque marker, for fluoroscopic visualization (i.e., contrast) as the inflation medium. Generally, a liquid fluid medium for expanding vascular balloons has been preferred because the expansion characteristics of a liquid are more uniform and predictable, and because a liquid medium is easier to work with and more familiar to the doctors. In the case of angioplasty balloons, for example, high pressure requirements (up to 20 atmospheres) necessitate that the inflation fluid be an incompressible fluid for safety reasons. While having numerous advantages, liquid fluids do not lend themselves to rapid deflation of an occlusive balloon because of the high resistance to movement of the liquid in a long small diameter tube. In the context of angioplasty procedures, the balloon catheter has a much larger lumen than a guidewire. Consequently, rapid deflation is possible. In the context of a guidewire, however, liquid-filled occlusive balloons typically cannot be deflated in less than a minute and, depending upon the length of the guidewire, can take up to several minutes to deflate. Consequently, it is not practical to shorten the period of total blockage of a vessel by repeatedly deflating and then re-inflating a liquid-filled occlusive balloon at the end of a guidewire.

Gas-filled balloons have been used for intra-aortic occlusive devices where rapid inflation and deflation of the occlusive device is required. Examples of such intra-aortic occlusive devices are shown in U.S. Pat. Nos. 4,646,719, 4,733,652, 5,865,721, 6,146,372, 6,245,008 and 6,241,706. While effective for use as an intra-aortic occlusive device, these occlusive devices are not designed for use as a guidewire as there is no ability to track a catheter over the intra-aortic occlusive device.

An early catheter balloon device that utilized a gas as an inflation medium and provided a volume limited syringe injection system is described in U.S. Pat. No. 4,865,587. More recently, a gas-filled occlusive balloon on a guidewire is described as one of the alternate embodiments in U.S. Pat. No. 6,217,567. The only suggestion for how the guidewire of the alternate embodiment is sealed is a valve-type arrangement similar to the valve arrangement used in a liquid fluid embodiment. A similar gas-filled occlusive balloon has been described with respect to the Aegis Vortex™ system developed by Kensey Nash Corporation. In both U.S. Pat. No. 6,217,567 and the Aegis Vortex™ system, the gas-filled occlusive balloon is used for distal protection to minimize the risk of embolization while treating a blocked saphenous vein coronary bypass graft. Once deployed, the occlusive balloon retains emboli dislodged by the atherectomy treatment process until such time as the emboli can be aspirated from the vessel. No specific apparatus are shown or described for how the gas is to be introduced into the device or how the occlusive balloon is deflated.

Although the use of occlusive devices has become more common for distal embolization protection in vascular procedures, particularly for treating a blocked saphenous vein coronary bypass graft, all of the existing approaches have significant drawbacks that can limit their effectiveness. Liquid-filled occlusive balloons can remain in place too long and take too long to deflate, increasing the risk of damages downstream of the occlusion. Occlusive filters are designed to address this problem, but suffer from blockage problems and can be complicated to deploy and retrieve and may allow small embolic particles to migrate downstream. Existing gas-filled occlusive balloons solve some of the problems of liquid-filled occlusive balloons, but typically have utilized complicated valve and connection arrangements. It would be desirable to provide for an occlusive device that was effective, simple, quick to deploy and deflate, and that could overcome the limitations of the existing approaches.

It would be even more desirable if a medical device, such as an inflation/deflation system and a sealing system for occlusive balloons which systems are intended for use with a biocompatible gas and intended to avoid oxygen exposure could be stored and then used with confidence that they have not been exposed to oxygen. Moreover, it would be still more desirable if any unintended oxygen exposure could be readily visually detected immediately upon opening a sealed container in the course of medical treatment.

SUMMARY OF THE INVENTION

In some embodiments, the present invention is directed toward a method and packaging system or storage arrangement including a container and an oxygen-sensitive material that is suitable for detecting the presence of oxygen inside the container after the container has been irradiated with radiation. In addition, at least some of the oxygen-sensitive materials of the present invention can be incorporated into component parts for some other devices, such as medical devices. By using the oxygen-sensitive material as a component piece of a medical device, or other device, the device itself becomes an oxygen indicator, thereby removing any ambiguity regarding the contact of the device with the ambient atmosphere. Furthermore, some of the oxygen-sensitive materials of the present invention can be stored in oxygen-rich environments because they do not become "active" until the oxygen-sensor material has been exposed to radiation. In some embodiments, the oxygen-sensitive materials are activated in an oxygen-free environment. As used in this application, the term "activated" or "active" means that the oxygen-sensitive material will undergo a visual change when exposed to oxygen. Thus, the present invention creates an effective storage arrangement having means for detecting the presence of oxygen, and ultimately for determining a failure in packaging, in applications involving radiation sterilization.

In one embodiment of the present invention, a sealable container adapted to isolate the contents thereof from the ambient atmosphere is provided with an oxygen-sensitive material located within the sealable container. The oxygen-sensitive material can be any material that undergoes a visual change when in contact with oxygen after the oxygen-sensitive material has been irradiated with gamma radiation in an oxygen-free environment.

In another embodiment of the present invention, a medical device is provided that contains a structural element which is composed of an oxygen-sensitive polymeric material. The oxygen-sensitive polymeric material will visually indicate if the medical device has been exposed to oxygen. Thus, in this embodiment of the present invention, the product, i.e., the medical device and the oxygen-sensitive material, is a single unit. In a further embodiment of the present invention, a medical device comprising a polycarbonate material is provided. The polycarbonate material used in this embodiment of the present invention will visually indicate the presence of oxygen after being irradiated with gamma radiation if oxygen is present.

In a method according to the present invention, an oxygen-sensitive storage arrangement is produced by placing an oxygen-sensitive material inside a sealable container. The oxygen-sensitive material can be any material that undergoes a visual change with oxygen after the oxygen-sensitive material has been irradiated with radiation. The atmospheric contents of the sealable container are then removed and the sealable container is sealed to isolate the oxygen-sensitive material inside the sealable container. The sealable container is then irradiated with an effective amount of radiation so that the oxygen-sensitive material will undergo a visual change if the oxygen-sensitive material contacts oxygen.

In another embodiment, the present invention is a gas inflation/evacuation system and sealing system for use with occlusive devices in vascular procedures. The gas inflation/evacuation system is removably connectible to the proximal end of a tubular guidewire assembly that has a distal portion and a proximal portion with an extended sealable section and includes an evacuation syringe to evacuate the tubular guidewire assembly and an inflation syringe or syringes for introducing a gas under pressure into the tubular guidewire assembly to inflate an occlusive balloon or other occlusive device proximate the distal end of the tubular guidewire assembly a plurality of times. A sealing system is also removably connectible to the proximal end of the tubular guidewire assembly and selectively seals the tubular guidewire assembly at one of a plurality of separate locations along the extended sealable section to form an airtight seal of the tubular guidewire assembly. Each time a deflation of the occlusive balloon is desired in order to reestablish blood flow to the vessel downstream of the occlusive balloon, the proximal end of the extended sealable section preferably is cut distal to the location of the last seal to quickly deflate the occlusive balloon.

The advantage of the gas inflation/evacuation system and sealing system of the present invention is that the occlusive device can be repeatably inflated and deflated a plurality of times during a vascular procedure in between which the proximal end of the tubular guidewire assembly is free of mechanical connections and obstructions and, therefore, the tubular guidewire assembly can function as a conventional exchange guidewire assembly for one or more over-the-wire catheters. Alternatively, the tubular guidewire assembly can be shorter in length for use with rapid exchange catheter systems. Unlike operation of existing liquid-filled occlusive devices, the present invention enables repeated and quick inflation and deflation which allows an operator to deploy the gas-filled occlusive device numerous times during a procedure for shorter periods of time, thereby reducing the risk of potential damage to downstream tissue. Unlike operation of other gas-filled occlusive devices, the simplicity of the present invention permits the tubular guidewire assembly to be used as a conventional exchange guidewire assembly. There are no complicated mechanical arrangements or valve systems internal to the tubular guidewire assembly that increase the cost, complexity, and potential for failure of the system.

In another preferred embodiment, the extended sealable section is an extended crimpable section and the sealing system includes a crimping mechanism. The extended crimpable section has a sufficient length to permit a plurality of crimps and cuts along the extended crimpable section and preferably has an outer diameter that is smaller than the outer diameter of the main body portion of the guidewire assembly. The crimping mechanism is used to crimp the extended crimpable section of the guidewire assembly to seal the guidewire assembly a plurality of times. Preferably, the gas inflation/evacuation system and the crimping mechanism and sealing mechanism of the sealing system constitute a handheld apparatus. Each time a deflation of the occlusive device is desired in order to reestablish blood flow to the vessel downstream of the occlusive device, the extended crimpable section is cut distal to the location of the last crimp so as to quickly deflate the occlusive device. Preferably, the extended crimpable section of the guidewire assembly is dimensioned and the crimping mechanism is arranged such that an effective outer diameter of the extended crimpable section at the location of a seal is no greater than the outer diameter of the main body portion of the guidewire assembly when the extended crimpable section is sealed.

In another alternate embodiment, the sealing mechanism is a plugging mechanism that selectively inserts a plug of material into the proximal end of the extended sealable section while maintaining an airtight seal between the guidewire assembly and the gas inflation/evacuation system. In one embodiment, the plug of material includes a wax/gel material and the sealing system includes wiping structure to remove excess wax/gel material from the outside of the extended sealable section once the wax/gel material has been inserted. In this embodiment, the extended sealable section may be opened either by cutting the extended sealable section distal to the location of the seal or by heating the proximal end of the extended sealable section.

In one embodiment for coronary vascular procedures, the guidewire assembly preferably has an effective length of at least 40 cm and more preferably at least 100 cm and an outer diameter of less than 0.060 inch and more preferably less than 0.018 inch, the extended sealable section has an effective length of at least 1 cm and more preferably at least 5 cm and an outer diameter of less than 0.050 inch and more preferably less than 0.012 inch, and the occlusive device (balloon) is deflated in less than two minutes and more preferably less than one minute. This embodiment is particularly adapted to provide distal embolization protection in debulking vascular interventional procedures, such as those involving a blocked saphenous vein coronary bypass graft. Alternatively, the guidewire assembly may be configured and dimensioned for use in peripheral vascular procedures or neurovascular procedures.

In a preferred embodiment, the inflation system of the gas inflation/evacuation system includes a plurality of individually actuatable syringes each containing a sufficient volume of biocompatible gas for a single inflation of the occlusive device so as to minimize the volume of biocompatible gas in the gas inflation/evacuation system in the event of a leak. The preferred embodiment is packaged in a sterile packaging that is assembled and packaged in a sealed chamber filled with a biocompatible gas such that any gas within the sterile packaging once packaged is only the biocompatible gas. In a particularly preferred embodiment, inflation/deflation systems and sealing systems are packaged in a container with the capability to detect undesired oxygen exposure, especially post radiation-sterilization, when a seal has been presumed to be effective.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIGS. 6, 6a and 6b are top views of two distal occlusion inflation devices each containing a component piece comprising an oxygen-sensitive material, with the device of FIG. 6b having just been exposed to air and with the device of FIG. 6a having been exposed to air for one week and thereby illustrating the color change associated with an oxygen-sensitive material of the present invention;

FIGS. 7, 7a and 7b are top views of two crimper devices that show a visual change associated with one embodiment of the present invention, with the device of FIG. 7b having just been exposed to air and with the device of FIG. 7a having been exposed to air for one week;

FIG. 8 is a schematic diagram of a guidewire occlusion system incorporating the present invention and operating in an evacuation mode;

FIG. 10a is a side view of the guidewire assembly shown in FIG. 8, and FIG. 10b is an enlarged view of the portion of FIG. 10a delineated by the circle 10b;

FIGS. 11a and 11b are fragmentary cross sectional views of different manners of joining the extended sealable section to the main body portion at the proximal portion of the guidewire assembly of FIG. 10a;

DETAILED DESCRIPTION OF THE PREFERRED EMBODIMENTS

In one embodiment of the present invention, a packaging system or storage arrangement is provided that comprises a sealable container adapted to isolate the contents of the sealable container from the ambient atmosphere. In this embodiment, an oxygen-sensitive material is located inside the sealable container. The oxygen-sensitive material can undergo a visual change upon contact with oxygen after the oxygen-sensitive material has been irradiated with radiation in the absence of oxygen. In one embodiment, the visual change is a color change. In some embodiments, the sealable container can isolate a medical product from the ambient atmosphere, while in other embodiments the sealable container can isolate a food product. In one embodiment, the sealable container isolates a distal occlusion inflation device from the ambient atmosphere. In some embodiments, the oxygen-sensitive material comprises a polycarbonate material. In one embodiment, the polycarbonate material comprises Dow Calibre® 2081 polycarbonate material. In some embodiments, the sealable container is resealable, while in other embodiments the sealable container is not resealable. In some embodiments, the sealable container is substantially free of oxygen. In one embodiment, the sealable container is a foil pouch.

In another embodiment of the present invention, a medical device comprising a structural element is provided. The structural element comprises an oxygen-sensitive polymeric material that can visually indicate if the medical device has been exposed to oxygen. In one embodiment, the medical device is a distal occlusion inflation device. In some embodiments, the oxygen-sensitive polymeric material can visually indicate the presence of oxygen after the oxygen-sensitive polymeric material has been irradiated by an effective amount of radiation. In one embodiment, the oxygen-sensitive polymeric material comprises Dow Calibre® 2081. In some embodiments, the radiation is gamma radiation, while in other embodiments the radiation is X-ray radiation. When the oxygen-sensitive polymeric material comprises Dow Calibre® 2081, an effective amount of gamma radiation is from about 25 Kilograys to about 45 Kilograys. In some embodiments, the structural element is attached to a background material which enhances visibility of the visual indication of the presence of oxygen.

In another embodiment, a storage arrangement comprising a sealable container and an oxygen-sensitive material is provided. In this embodiment, the oxygen sensitive material will not function as an oxygen detector until the oxygen-sensitive material has been activated. In some embodiments, the oxygen-sensitive material can be activated by irradiating the oxygen-sensitive material with radiation in an oxygen-free environment. In one embodiment, the oxygen-sensitive material is activated by irradiating the material with gamma radiation.

Figure 1:
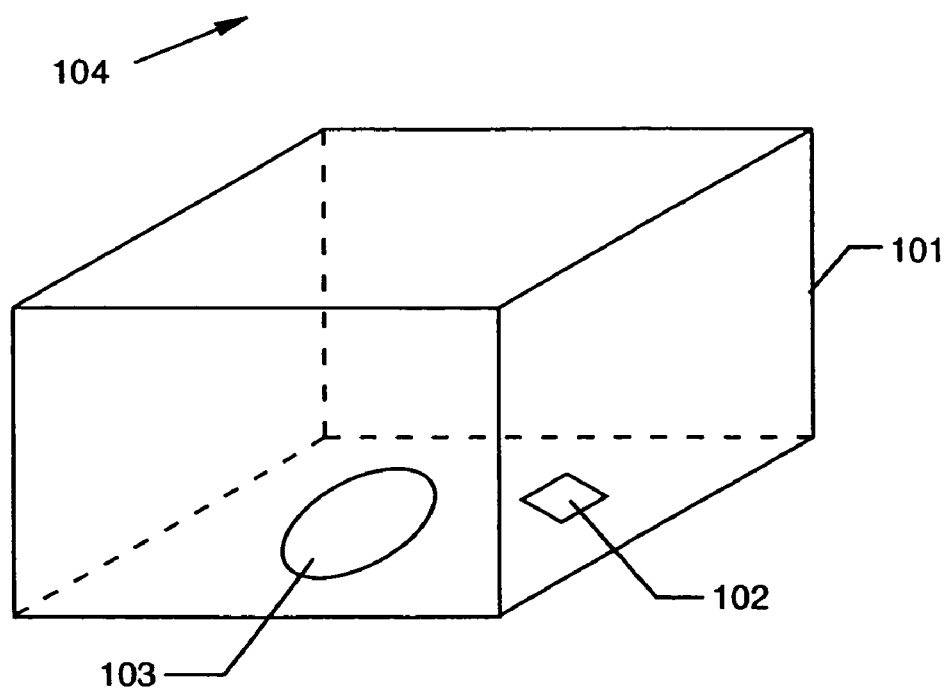
FIG. 1 is a schematic perspective view of one embodiment of a storage arrangement according to the present invention where a container and an oxygen-sensitive material are provided and where structures within the container have been made visible while hidden edges of the container are shown with phantom lines.

FIG. 1 shows schematically one embodiment of a packaging system or storage arrangement according to the present invention. As shown in FIG. 1, a sealable container 101 (depicted representatively) isolates a product 103 (also depicted representatively) from the ambient atmosphere 104. An oxygen-sensitive material 102 (illustrated representatively) is located inside the sealable container. The oxygen-sensitive material 102 can visually indicate the presence of oxygen inside the sealable container 101. In one embodiment, the visual indication of the presence of oxygen will be a change in color of the oxygen-sensitive material 102. The oxygen-sensitive material 102 of the present invention can be any material that will visually indicate the presence of oxygen after the oxygen-sensitive material 102 has been irradiated by radiation. A suitable choice for the oxygen-sensitive material 102 is a polycarbonate resin manufactured by Dow Chemical Company and sold under the trademark Dow Calibre® 2081. In one embodiment, when the oxygen-sensitive material 102 comprises Dow Calibre® 2081, the oxygen-sensitive material 102 will visually indicate the presence of oxygen after being irradiated with gamma radiation. A suitable amount of gamma radiation has been found to be from about 25 Kilograys to about 45 Kilograys. In other embodiments, the radiation used can be X-ray radiation.

Figure 2:
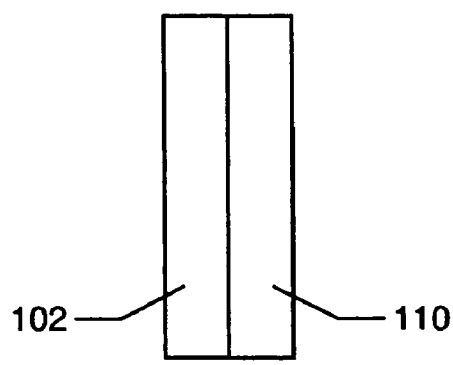
FIG. 2 is a side view of an oxygen-sensitive material attached to a background material that enhances the visual change of the oxygen-sensitive material.

The oxygen-sensitive material 102 as shown representatively in FIG. 1 can be formed into any desirable shape for use in the present invention. In one embodiment, the shape of the oxygen-sensitive material is a rectangular chip. As shown in FIG. 2, the oxygen-sensitive material 102 optionally can be attached to a background material 110 to enhance the visibility of the visual change of the oxygen-sensitive material 102. The background material can be composed of metal, plastic, paper, or any other suitable material that will enhance the visibility of the visual change. For example, a blue background material would make a yellow indicator appear green. Potential background materials could also have the word "exposed" written across the background material in a color such that upon contact with oxygen, the word "exposed" would become visible. As another option, the oxygen-sensitive material can be arranged to form at least one symbol that assists in interpreting the visual change of the oxygen-sensitive material. In embodiments that employ a background material 110, the background material 110 can be attached to the oxygen-sensitive material 102 through the use of generally known adhesives or mechanical fasteners.

The sealable container of the present invention as shown representatively at 101 in FIG. 1 can be composed of any substance that will transmit radiation and that is impermeable to gas, especially oxygen. Examples of suitable materials for the container are metals, glass, gas-impermeable plastics, gas-impermeable thermosets and rubbers, and gas-impermeable foil pouches. In one embodiment, the sealable container is a foil pouch of multi-layer construction comprising a silicone oxide treated PET layer, a foil layer, a biaxially oriented nylon layer, and a polyethylene layer. The gas-impermeable plastic containers of the present invention can be either rigid or flexible. Suitable plastic materials for the gas-impermeable plastic containers include, but are not limited to, gas-impermeable polyethylenes, polystyrenes, polycarbonates, nylons and polyethylene terephthalates. Potential thermoset and rubber materials for the sealable containers include gas-impermeable phenol formaldehydes, urea formaldehydes, natural rubbers and nitrile rubbers.

Figure 3:
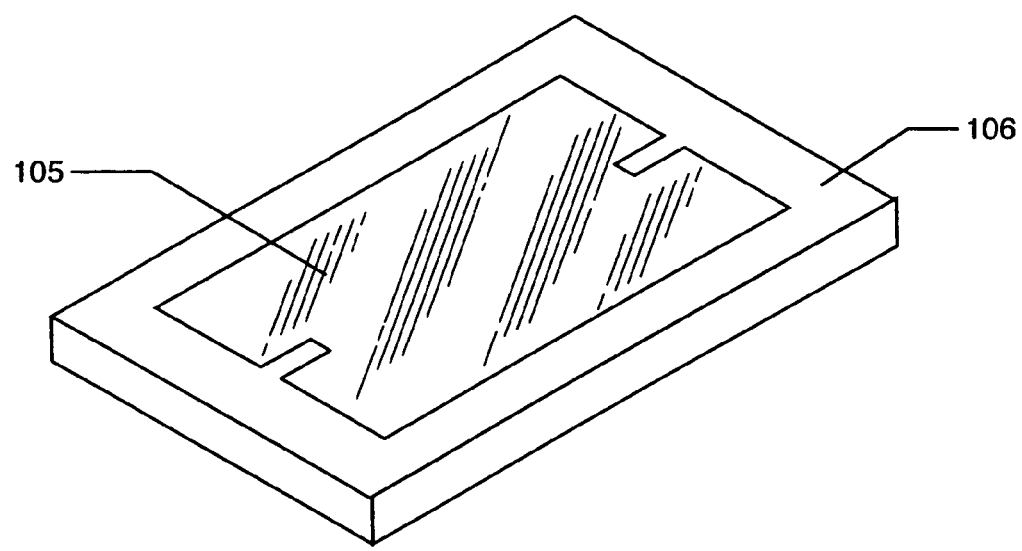
FIG. 3 is a perspective view of one embodiment of a storage container of the present invention.
Figure 4:
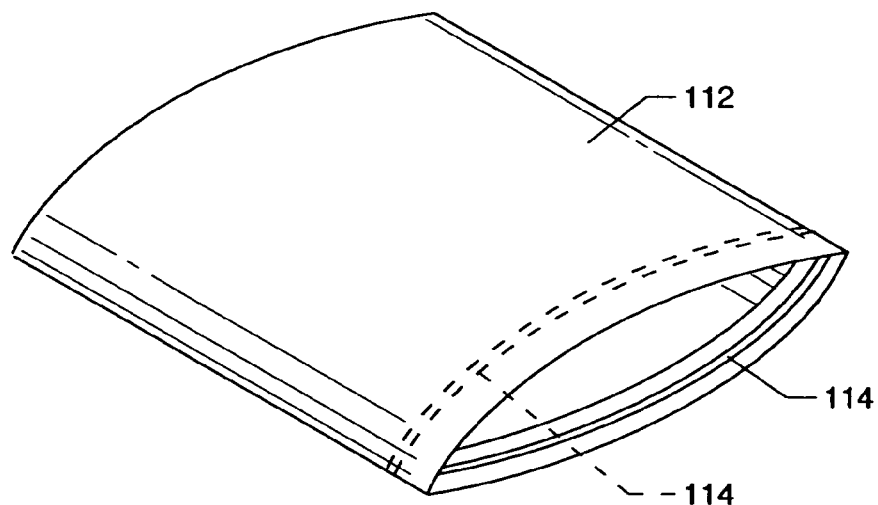
FIG. 4 is a view of a resealable container that can be used in the present invention.
Figure 5:
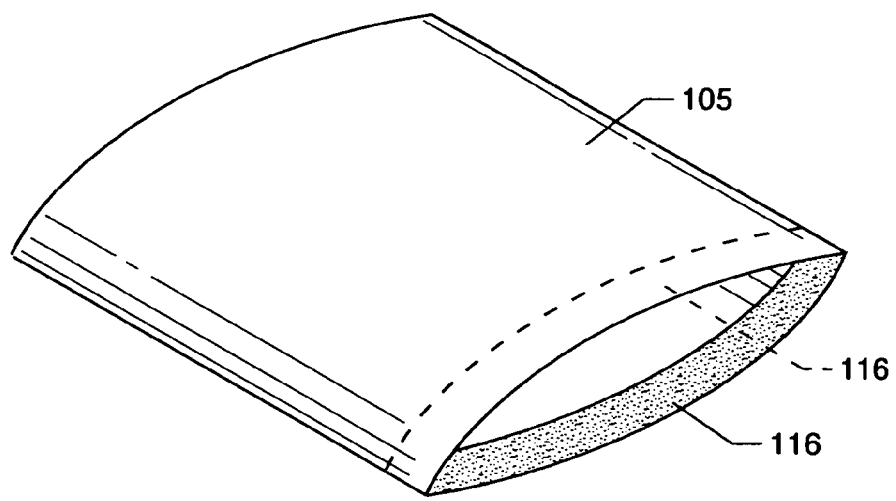
FIG. 5 is a view of a foil pouch showing a plastic coating that can be heated to seal the foil pouch.

The sealable container 101 shown representatively in FIG. 1 can be sealed by any conventional means known to be used in the packaging industries including thermal seals, adhesive seals, or airtight mechanical closures such as caps or lids; and the sealable container can be a container that is resealable or a container that is not resealable. As shown in FIG. 3, one specific embodiment of the sealable container 101 shown in FIG. 1 is a gas-impermeable foil pouch 105 with a protective cardboard packaging 106. FIG. 4 shows another example comprising a resealable pouch 112 with closure means 114 on at least one end of the resealable pouch 112 that permits the resealable pouch 112 to be optionally resealed. When the sealable container is a gas-impermeable foil pouch 105, a heat sealer can be used to heat plastic coatings located on the inside top and bottom of the foil pouch. FIG. 5 shows one embodiment of foil pouch 105 with plastic coatings 116 located on the inside top and bottom of the foil pouch 105. Heating will cause the plastic coatings on the top and bottom to flow together and seal the foil pouch 105.

The product 103 contained within the sealable container 101 can be any product in which a controlled oxygen-free environment is desirable or necessary. Suitable products for the present invention include, but are not limited to, medical devices, pharmaceuticals, and food products.

In one embodiment, a storage arrangement is provided that comprises a sealable container 101 and an oxygen-sensitive material. In this embodiment, the oxygen-sensitive material will not function as an oxygen indicator until the oxygen-sensitive material has been activated. One method of activating the oxygen-sensitive material is by irradiating the material. In some embodiments, suitable forms of radiation for activating the oxygen-sensitive material include gamma radiation and X-ray radiation. In one embodiment, the oxygen-sensitive material comprises Dow Calibre® 2081 polycarbonate resin. When the oxygen-sensitive material comprises Dow Calibre® 2081, a dose of gamma radiation from about 25 Kilograys to about 45 Kilograys will activate the material. While not wanting to be limited to a particular theory, it is believed that the oxygen-sensitive property of the Dow Calibre® 2081 material is likely due to the dye used to color the material or the stabilizers used to protect the material from degradation.

Figure 6A:
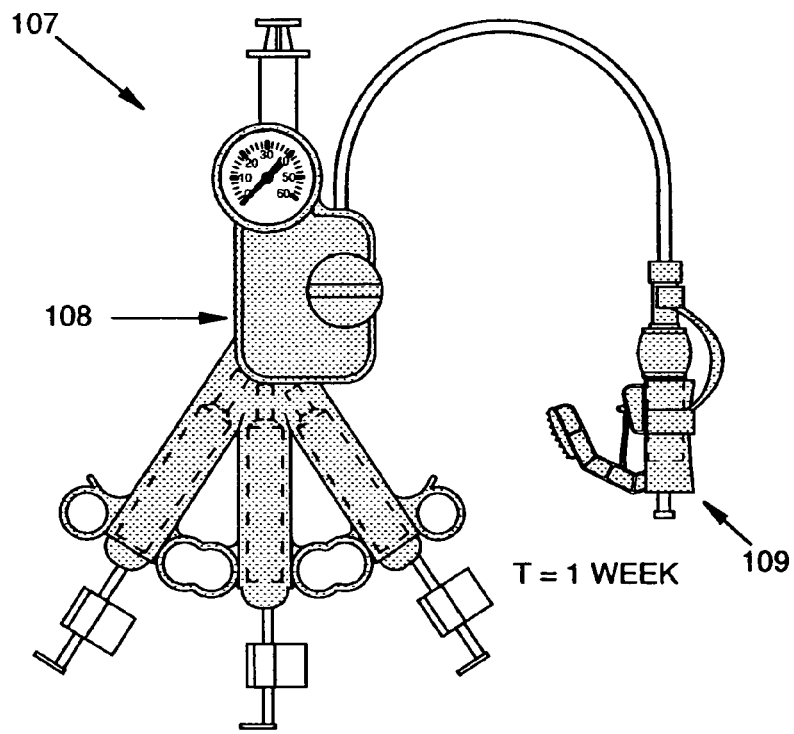
Figure 6B:
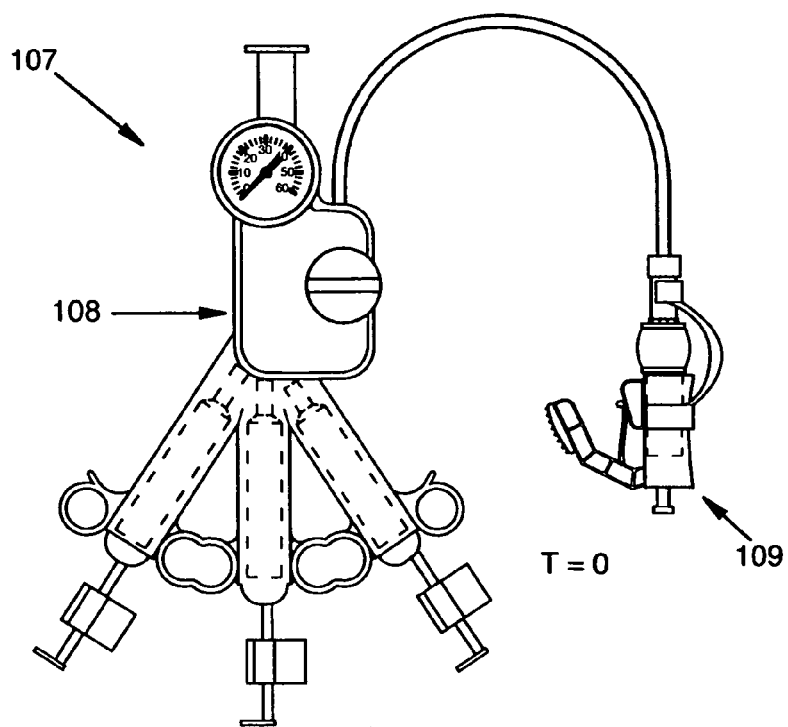

In another embodiment of the present invention, a medical device within a container contains a component piece that is composed of an oxygen-sensitive polymeric material. FIGS. 6a and 6b show one possible embodiment where a medical device 107 has a component piece that is composed of an oxygen-sensitive polymeric material. The medical device 107 is a distal occlusion inflation device available under the trademark GuardDOG which uses $CO_2$ as the inflation medium and which generally comprises a main body 108 and a crimper device 109. In this embodiment, both the crimper device 109 and the main body 108 are composed of an oxygen-sensitive polymeric material. One reason for using an oxygen-sensitive polymeric material in this application is because the inflation medium needs to be relatively free from oxygen in order to prevent the release of oxygen or ambient air into the blood stream in the event that the distal occlusion inflation device would burst, thereby causing a potential embolism. By using $CO_2$ as the inflation medium, the inflation gas can be easily absorbed into the blood stream in the event that the inflation device fails. The oxygen-sensitive polymeric material permits the operator to confirm that the gas within the device that will be used to inflate the inflation device does not include any significant amount of oxygen prior to the use of the device.

In one embodiment, the oxygen-sensitive polymeric material is composed of Dow Calibre® 2081 polycarbonate resin. When a medical device with an oxygen-sensitive polymeric component piece comprising Dow Calibre® 2081 is irradiated with gamma radiation, in the absence of oxygen, the oxygen-sensitive material becomes activated and will undergo a visual change if oxygen contacts the material. In one embodiment, the visual change, or indication, is a color change. It has been found that from about 25 Kilograys to about 45 Kilograys of gamma radiation will activate Dow Calibre® 2081.

An example of the visual change, which indicates the presence of oxygen, associated with this embodiment of the present invention can be seen in FIGS. 6a and 6b by comparing the color of the main body 108 and the crimper device 109 of the medical device 107 shown in FIG. 6a with the color of the main body 108 and the crimper device 109 of the medical device 107 shown in FIG. 6b, the stippling in FIG. 6a representing a change in color from the showing in FIG. 6b. The elapsed time, after exposure to oxygen, before a visible change can be detected is generally 1-8 hours, preferably 1-2 hours. As shown by FIGS. 6a and 6b, when a component piece of a medical device is composed of an oxygen-sensitive polymeric material, the device itself becomes an oxygen indicator, and any ambiguity about whether the device has been exposed to oxygen is removed.

The method for producing the storage arrangement of the present invention involves placing an oxygen-sensitive material 102, for example, Dow Calibre® 2081 polycarbonate resin, inside a gas-impermeable sealable container 101. In some embodiments, a product 103, such as, for example, a medical product or food product, will also be placed into the sealable container 101. In one embodiment, the sealable container is a foil pouch 105. As discussed above, the oxygen-sensitive material 102 can be any material that visually indicates the presence of oxygen after exposure to radiation. As discussed above, the oxygen-sensitive material 102 can comprise a polycarbonate resin. Furthermore, the oxygen-sensitive material 102 may be formed into any desired shape or size depending upon the application.

Before being placed inside the sealable container, the oxygen-sensitive material 102 optionally can be attached to a background material 110 to enhance the visibility of the visual change. In addition, the oxygen-sensitive material 102, and the optional background material 110, can be either fixed inside the container or can be free-moving inside the container. By fixed inside the sealable container 101, it is meant that the oxygen-sensitive material 102 is directly attached to the inside of the sealable container 101. In embodiments where the oxygen-sensitive material is fixed inside the sealable container 101, any conventional method of attachment, including adhesives and mechanical fasteners, may be used that does not interfere with the function of the oxygen-sensitive material 102. Conversely, the term "free-moving" is intended to describe embodiments of the present invention where the oxygen-sensitive material 102 is not attached directly to the inside of the sealable container 101.

The atmospheric contents of the sealable container 101 are then removed by either vacuum or by purging the sealable container 101 with an inert gas such as nitrogen, carbon dioxide, argon or helium. In one embodiment, a vacuum is used to remove the atmospheric contents because a higher percent of oxygen, or atmospheric gas, can be removed in a shorter period of time as compared to purging. If the atmospheric contents of the container are removed by a vacuum, the sealable container 101 may be subsequently filled with an inert gas. In some embodiments, the ability of the oxygen-sensitive materials 102 to visually indicate the presence of oxygen is not dependent upon the choice of inert gas used as the controlled environment. Furthermore, the oxygen-sensitive materials 102 of the present invention can also function in applications where the controlled environment is a vacuum.

Once the atmospheric contents have been removed from the sealable container 101, the sealable container 101 will be substantially free of oxygen. As described above, the sealable container 101 can be filled with a substantially oxygen-free gas. The substantially oxygen-free gas can be nitrogen, helium, argon, carbon dioxide or some other inert gas. In some embodiments, the sealable container 101 is not filled with a substantially oxygen-free gas, and in those embodiments the controlled inert environment is a vacuum. The sealable container 101 is then sealed to isolate the oxygen-sensitive material 102 from the ambient atmosphere. As noted above, the sealable container 101 may be sealed by any conventional means known in the packaging industry including, but not limited to, thermal, adhesive or mechanical closures. In embodiments where the sealable container is a foil pouch 105, a heat press can be used to seal the foil pouch. The choice of sealing means will generally be determined by the particular choice of container being employed in a specific application.

The sealed container, including any contents or products contained within the sealed container, can then be irradiated with an effective amount of radiation to activate the oxygen-sensitive material 102. As discussed above, the sealable container can isolate foods, medical devices, pharmaceuticals, or other products from the ambient atmosphere. In some embodiments, the radiation used to activate the oxygen-sensitive material 102 is gamma radiation. In other embodiments of the present invention, the radiation used to activate the oxygen-sensitive material is X-ray radiation. In one embodiment, where the oxygen-sensitive material comprises Dow Calibre® 2081, an effective amount of gamma radiation to activate the oxygen-sensitive material has been found to be from about 25 Kilograys to about 45 Kilograys.

Figure 7A:
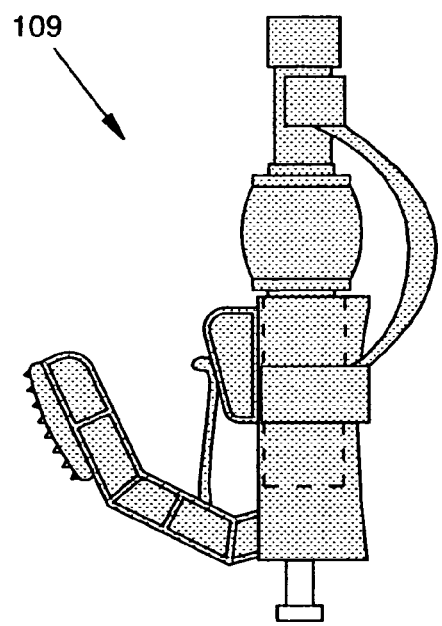
Figure 7B:
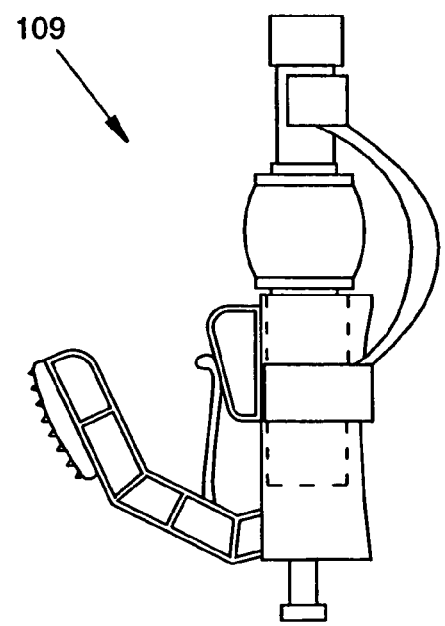

In the embodiment of the present invention where the oxygen-sensitive material 102 is Dow Calibre® 2081, the gamma radiation can visually change the oxygen-sensitive material 102 from a purple color to a yellow-gray color. In this embodiment, once this color change has occurred, the oxygen-sensitive material 102 has been activated. Once activated, the Dow Calibre® 2081 material will undergo a visual color change when exposed to oxygen. Prior to being activated, some of the oxygen-sensitive materials 102 of the present invention will not undergo a visual change when exposed to oxygen. As a result, some of the unactivated oxygen-sensitive materials of the present invention can be handled and stored in oxygen-rich environments. This feature of the oxygen-sensitive materials of the present invention facilitates easier storage and processing of the sensor materials as compared to other chemical oxygen indicators. FIGS. 7a and 7b show one example of a visual change associated with one embodiment of the present invention involving crimper devices 109 formed of oxygen-sensitive material where the oxygen-sensitive material comprises Dow Calibre® 2081. The crimper device 109 shown in FIG. 7a has been exposed to oxygen for one week, while the crimper device 109 shown in FIG. 7b has just been removed from a substantially oxygen-free environment. The stippling in FIG. 7a represents a change in color from the showing in FIG. 7b.

The embodiments are intended to be illustrative and not limiting. Additional embodiments are within the claims. Although the present invention has been described with reference to particular embodiments, workers skilled in the art will recognize that changes may be made in form and detail without departing from the spirit and the scope of the invention.

Figure 9:
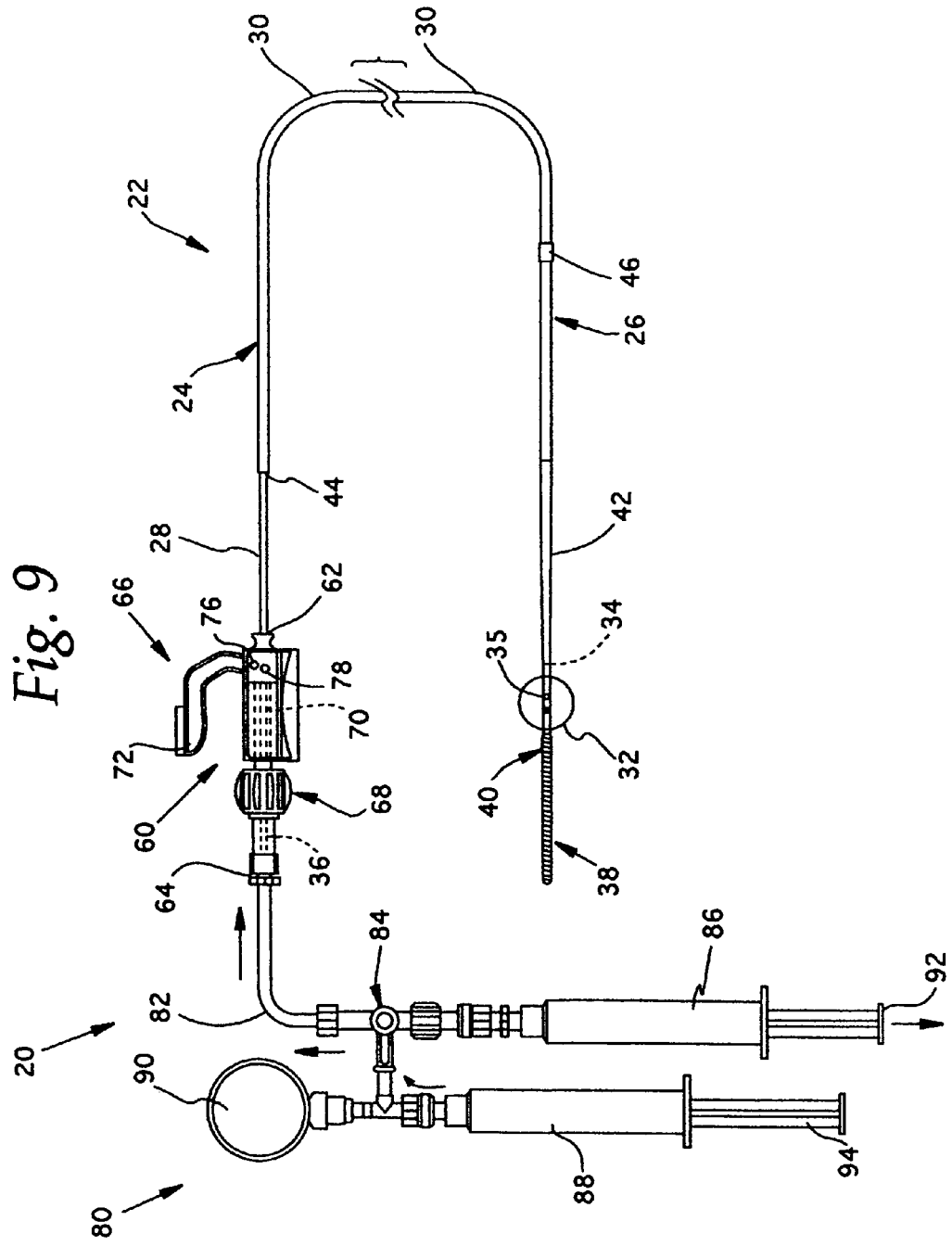
FIG. 9 is a schematic diagram of the guidewire occlusion system shown in FIG. 8 operating in an inflation mode.

Referring now to FIGS. 8 and 9, the overall structure and operation of a guidewire occlusion system 20 incorporating the present invention will be described. The guidewire occlusion system 20 includes a guidewire assembly 22, a sealing system 60, and a gas inflation/evacuation system 80. The preferred embodiments of the overall guidewire occlusion system 20 are described in further detail in the previously identified co-pending application Ser. No. 10/012,903 entitled "Guidewire Occlusion System Utilizing Repeatably Inflatable Gas-Filled Occlusive Device" filed Nov. 6, 2001, patented Aug. 23, 2005, as U.S. Pat. No. 6,932,828.

Guidewire assembly 22 is a tubular member that includes a proximal portion 24 and a distal portion 26. As used in the present invention, the terms proximal and distal will be used with reference to an operator, such that a distal portion of the guidewire assembly 22, for example, is the portion first inserted into a blood vessel, and the proximal portion remains exterior to the patient and is therefore closer to the operator. An extended sealable section 28 is provided proximate the proximal portion 24 of guidewire assembly 22.

Preferably, the extended sealable section 28 is an extended crimpable section comprised of a tubular segment having an outer diameter smaller than an outer diameter of a main body portion 30 of guidewire assembly 22. Although the diameter of the extended crimpable section could be any size consistent with effective use as a guidewire, it will be understood that the smaller diameter allows for less force to be used in sealing the extended crimpable section and provides a crimped seal that is not too large when crimped. An occlusive balloon 32 is located along the distal portion 26 of guidewire assembly 22. The occlusive balloon 32 is fluidly connected via a lumen 34 to the proximal end 36 of guidewire assembly 22, with channels or holes 35 allowing for fluid communication between lumen 34 and occlusive balloon 32. In a preferred embodiment, a flexible tip 38 is positioned at the distal end 40 of distal portion 26 of the guidewire assembly 22. Preferably, distal portion 26 of guidewire assembly 22 includes a tapered portion 42 to increase the flexibility and transition properties of the distal portion 26 of guidewire assembly 22.

Preferably, sealing system 60 is implemented as part of a handheld apparatus that also includes gas inflation/evacuation system 80. Alternatively, sealing system 60 may be a handheld unit completely separate from the gas inflation/evacuation system 80. Sealing system 60 includes a first aperture 62 into which the proximal end 36 of guidewire assembly 22 is insertable so as to operably position at least a portion of extended sealable section 28 in relation to sealing system 60. Sealing system 60 further includes a second aperture 64 that is fluidly connectible to gas inflation/evacuation system 80. The sealing system 60 includes means for selectively sealing the extended sealable section which in the preferred embodiment comprises a crimping mechanism 66 and a sealing mechanism 68. A passageway 70 is defined from first aperture 62 to second aperture 64 and extends through both crimping mechanism 66 and sealing mechanism 68. Preferably, at least a portion of the extended sealable section 28 is inserted into first aperture 62 a sufficient distance to engage crimping mechanism 66 and sealing mechanism 68.

Figure 19:
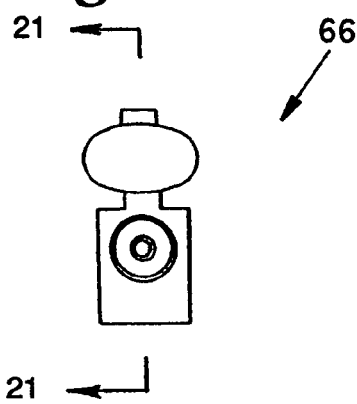
FIG. 19 is an end view of a crimping mechanism.
Figure 20:
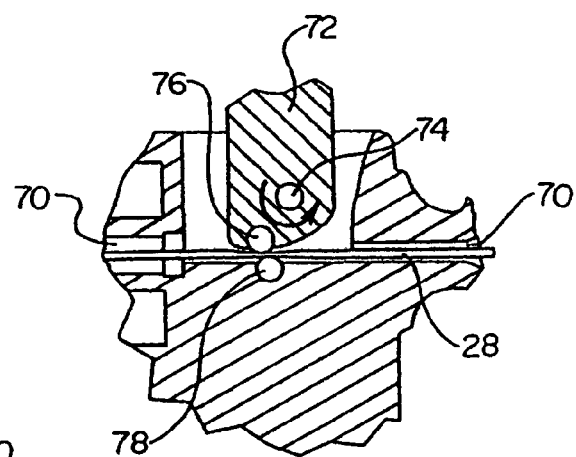
FIGS. 20 and 21 are two sectional views of the crimping mechanism of FIG. 19, FIG. 21 being a view taken along the line 21-21 of FIG. 19, and FIG. 20 being a magnification of the portion of FIG. 21 indicated by the dashed circle.
Figure 21:
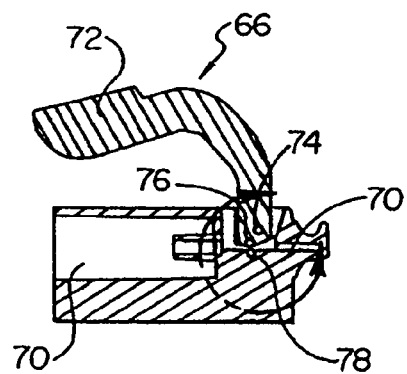

In a preferred embodiment of the crimping mechanism 66 as shown in FIGS. 19-21, the crimping mechanism 66 comprises a handle 72 that actuates a pivotable cam arrangement 74 that crimps and then severs the extended sealable section 28 between a pair of rollers 76, 78 by mechanically flattening and pinching the extended sealable section 28 to the point of breaking. Preferably, the sealing mechanism 68 has a rotatable hemostatic valve positioned proximal to the crimping mechanism 66 along passageway 70. Preferably, crimping mechanism 66 and sealing mechanism 68 are arranged coaxially with each other along a straight portion of passageway 70. In this embodiment, when the proximal end 36 of guidewire assembly 22 is inserted into first aperture 62 until the proximal end 36 engages the hemostatic valve of sealing mechanism 68, the extended sealable section 28 is properly positioned relative to the crimping mechanism 66.

It will be seen that the relative distance between the engaging portions of sealing mechanism 68 and crimping mechanism 66 in this embodiment effectively defines the relative distances between a plurality of locations along extended sealable section 28 at which an airtight seal can be created, as shown in FIGS. 8-9. To permit multiple inflations and deflations of the occlusive balloon 32 of the guidewire assembly 22, the length of the extended sealable section 28 should be greater than at least twice the distance between crimping mechanism 66 and sealing mechanism 68.

The gas inflation/evacuation system 80 is connected via conduit 82 to the second aperture 64 of the sealing system 60. The gas inflation/evacuation system 80 preferably includes a valve arrangement 84 that selectively couples one of an evacuation system which includes means for evacuating the guidewire assembly 22 and an inflation system which includes means for introducing a gas into the guidewire assembly 22 to the conduit 82. The evacuation system includes an evacuation syringe 86 which is used to evacuate the guidewire assembly 22, passageway 70, and conduit 82. The inflation system includes an inflation syringe 88 which contains a volume of a biocompatible gas sufficient to inflate the occlusive balloon 32 a plurality of times. Preferably, the biocompatible gas is carbon dioxide. Other biocompatible gasses that may be utilized with the present invention include oxygen, nitrogen, and nitrous oxide. Although not preferred, low viscosity biocompatible liquids or foams also may be used for inflation provided the surface tension of the fluid is sufficient to permit the rapid inflation and deflation contemplated by the present invention. Optionally, a pressure gauge 90 can be associated with the inflation syringe 88.

In a preferred embodiment shown in FIGS. 10a, 10b, 11a and 11b, guidewire assembly 22 is constructed as described in further detail in the previously identified co-pending application Ser. No. 10/012,891 entitled "Guidewire Assembly Having Occlusive Device And Repeatably Crimpable Proximal End" filed Nov. 6, 2001, currently pending. The main body portion 30 is formed of a primary stainless steel hypotube having an outer diameter of 0.013 inch and an inner diameter of 0.007 inch. To accomplish passive deflation in the desired time of less than one minute when the extended sealable section 28 is cut, it is preferable that the main body portion 30 have an inner diameter of at least 0.002 inch. The extended sealable section 28 of guidewire assembly 22 is comprised of a crimp tube also formed of stainless steel and having an outer diameter of 0.009 inch to 0.015 inch and an inner diameter of at least 0.002 inch and preferably about 0.005 inch. The extended sealable section 28 is preferably a separate piece secured to the proximal portion 24 by a laser weld 44 (see FIGS. 8, 9 and 10a) of sufficient strength. Alternatively, the extended sealable section 28 may be formed by centerless grinding or reducing the outer diameter of a portion of the proximal portion 24 of the main body portion 30 of guidewire assembly 22. Still other embodiments may enable the extended sealable section to be a modified, treated or otherwise fabricated portion of the proximal portion 24 of the main body portion 30 of guidewire assembly 22 that is suitable for the particular sealing technique to be used. As shown in FIG. 11a, in one embodiment the distal end of the extended sealable section 28 is preferably centerless ground and press fit within a chamfered proximal end of the main body portion 30. Alternatively, as shown in FIG. 11b, a chamfered crimp arrangement could be used. Still further, a separate joining/crimping tube or other tubular joining arrangements could be used. Preferably, a protective polymer coating 56 of polytetrafluoroethylene (PTFE) or a hydrophilic coating is applied by any of a number of known techniques such that the coating 56 surrounds the main body portion 30. The protective polymer coating 56 is preferably about 0.0004+/−0.0003 inch thick such that the effective outer diameter of the main body portion 30 of guidewire assembly 22 is 0.0132-0.0144 inch.

In this embodiment, the extended sealable section 28 can be made of any material that when deformed and severed retains that deformation so as to form an airtight seal. When crimped and severed, it is preferable that the extended sealable section 28 not present a sharp, rigid point that is capable of piercing a gloved hand. It has been found that as long as the preferred embodiment is not gripped within less than one inch of the proximal end of the extended sealable section 28, the severed proximal end of the extended sealable section 28 does not penetrate a standard surgical glove. In addition, the extended sealable section 28 must have sufficient strength in terms of high tensile and kink resistance to permit catheter devices to repeatedly pass over the extended sealable section 28.

In this embodiment, the main body portion 30 is preferably secured to the distal portion 26 using a Ni—Ti alloy or stainless steel sleeve 46, or of other suitable material, laser welded to the main body portion 30 at laser weld 48 and crimped to the distal portion 26 at crimp 50. The distal portion 26 is preferably formed of a Ni—Ti alloy having an inner diameter of 0.0045 inch and an outer diameter that ranges from 0.014 inch to 0.0075 inch to form tapered portion 42, preferably formed by a centerless grinding process. Preferably, the distal portion includes a pair of coil sections, proximal tip coil 52 and distal tip coil 54, that are longitudinally spaced apart and adjacent to the holes 35 and that assist in providing a better surface for bonding the occlusive balloon 32 to the distal portion 26. This arrangement also tends to increase the visibility of the location of the occlusive balloon 32 under fluoroscopy, as the occlusive balloon 32 filled with a biocompatible gas will be radiotranslucent when compared to the two coils 52 and 54. Alternatively, a platinum markerband could be located around the distal portion 26 just proximal to the occlusive balloon 32 to serve as a radiopaque/MRI marker. The flexible tip 38 is a coiled tip attached to distal portion 26 distal to occlusive balloon 32, preferably by a crimp. Alternatively, a sleeve could be welded to the flexible tip 38, and the tapered portion 42 could then be inserted into this sleeve and crimped.

Alternatively, any number of other alloys or polymer materials and attachment techniques could be used in the construction of the guidewire assembly 22, provided the materials offer the flexibility and torque characteristics required for a guidewire and the attachment techniques are sufficiently strong enough and capable of making an airtight seal. These materials include, but are not limited to, Ni—Ti, 17-7 stainless steel, 304 stainless steel, cobalt superalloys, or other polymer, braided or alloy materials. The attachment techniques for constructing guidewire assembly 22 include, but are not limited to, welding, mechanical fits, adhesives, sleeve arrangements, or any combination thereof.

The occlusive balloon 32 may be made of any number of polymer or rubber materials. Preferably, the occlusive balloon is preinflated to prestretch it so that expansion is more linear with pressure. Preferably, the pressure supplied by gas inflation/evacuation system 80 is designed to stay well within the elastic limit of the occlusive balloon 32. A two-layer occlusive balloon arrangement, adding gas and/or liquid between balloon layers, may be used in an alternate embodiment to increase visibility of the distal end 40 of the distal portion 26 of the guidewire assembly 22 under fluoroscopy.

In practice, medical personnel gain entry to the vessel lumen prior to use of the guidewire occlusion system 20. The extended sealable section 28 of the proximal portion 24 of guidewire assembly 22 is inserted into first aperture 62 and connected via sealing mechanism 68. The distal portion 26 of guidewire assembly 22 is inserted into the vessel lumen, and occlusive balloon 32 is inserted to a point distal to the vessel occlusion. Valve arrangement 84 is set for evacuation. Evacuation syringe plunger 92 of evacuation syringe 86 is slidably withdrawn removing any air from guidewire assembly 22. Valve arrangement 84 is then set for inflation. Inflation syringe plunger 94 of inflation syringe 88 is slidably advanced inserting a volume of an inert gas into guidewire assembly 22. The inert gas inflates occlusive balloon 32 as shown in FIG. 9. During inflation, the medical personnel monitor pressure gauge 90 to ensure that the inflation pressure does not exceed the burst rating of the occlusive balloon 32 and to gauge the relative size of the occlusive balloon 32 as it is inflated. Following inflation of occlusive balloon 32, crimping mechanism 66 is employed to crimp the extended sealable section 28 of guidewire assembly 22, thereby sealing the guidewire assembly 22 to maintain the occlusive balloon 32 in an inflated state. Sealing mechanism 68 is released and the extended sealable section 28 is removed from first aperture 62 such that the proximal portion 24 of the guidewire assembly 22 is free of mechanical or other obstructions and can function as a conventional guidewire. When the medical personnel decide to deflate the occlusive balloon 32, the extended sealable section 28 is cut using a medical scissors or the like distal to the existing crimp in the extended sealable section 28. When the medical personnel deem reinflation of the occlusive balloon 32 to be necessary, the extended sealable section 28 of the proximal portion 24 is reinserted into first aperture 62. Sealing mechanism 68 is then reactivated and the evacuation/inflation process can be repeated. It will be understood that a crimping handle 72 may also be provided with a separate severing arrangement to cut the extended sealable section 28. Alternatively, extended sealable section 28 may be scored or otherwise weakened in selected locations to assist in crimping or severing, including severing by repeated bending back and forth at one of the scored locations. In another embodiment, the extended sealable section 28 could be broken off rather than sheared by using a brittle metal for the extended sealable section that aids in the severing of the extended sealable section 28.

Figure 12:
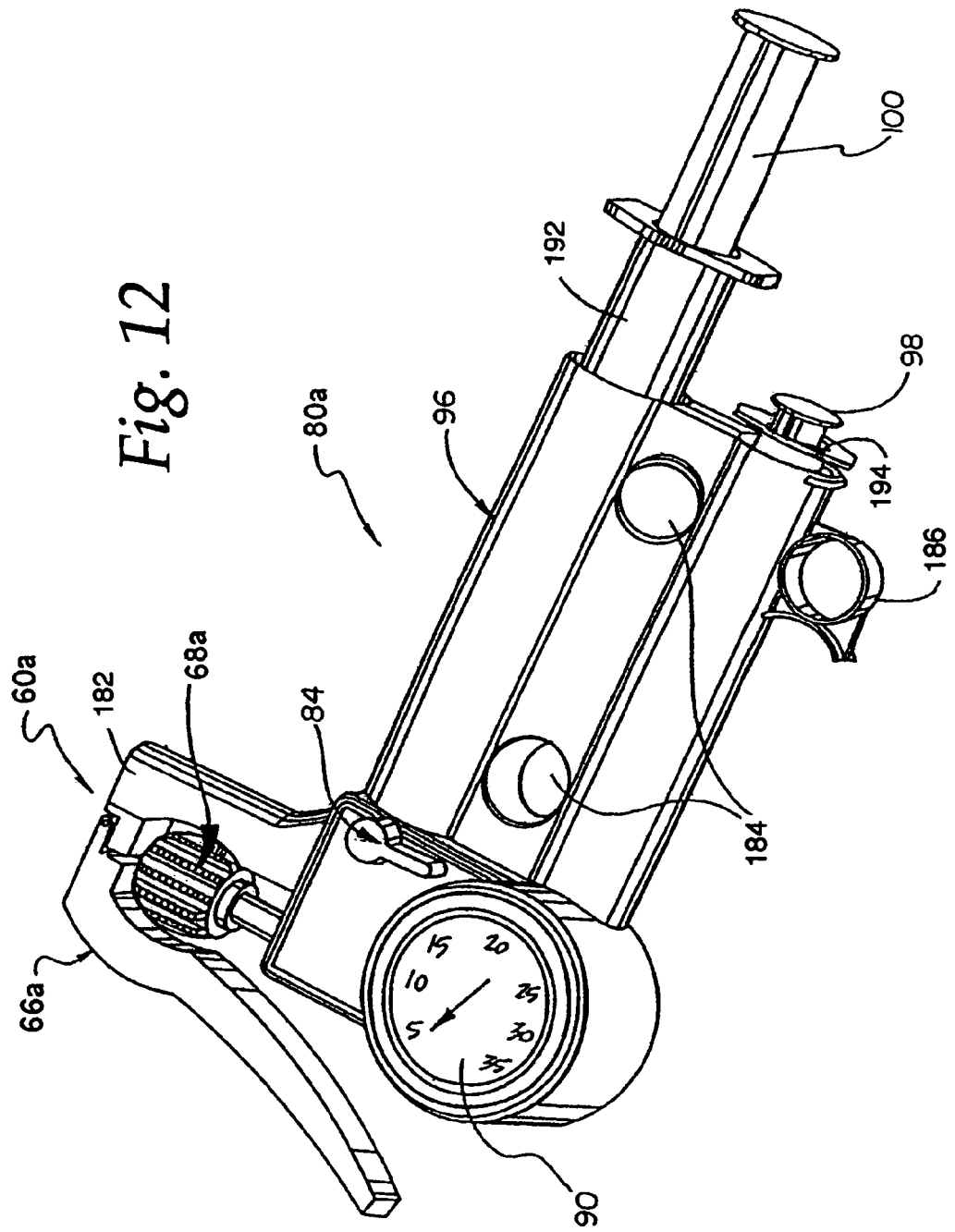
FIGS. 12-14 are perspective views of three alternate embodiments of gas inflation/evacuation systems and the sealing systems used therewith.

FIG. 12 shows an alternative unitized gas inflation/evacuation system 80a and also an alternative sealing system 60a. Assembly body 96 contains individual inflation syringe 194 with inflation syringe plunger 98 and individual evacuation syringe 192 with evacuation syringe plunger 100. Assembly body 96 contains pressure gauge 90. Attached to assembly body 96 is support structure 182 which supports a sealing system 60a that includes crimping mechanism 66a and sealing mechanism 68a. Valve arrangement 84 is mounted on the surface of assembly body 96. Assembly body 96 contains two fingergrip bores 184. Attached to assembly body 96 is fingergrip 186. In the preferred embodiment, the assembly body 96 is constructed of a suitable inert plastic polymer, although any polymer material used in construction of medical devices could be used. In another embodiment, the assembly body 96 can be constructed of suitable metal alloys or even of tempered glass or any combination thereof.

Figure 13:
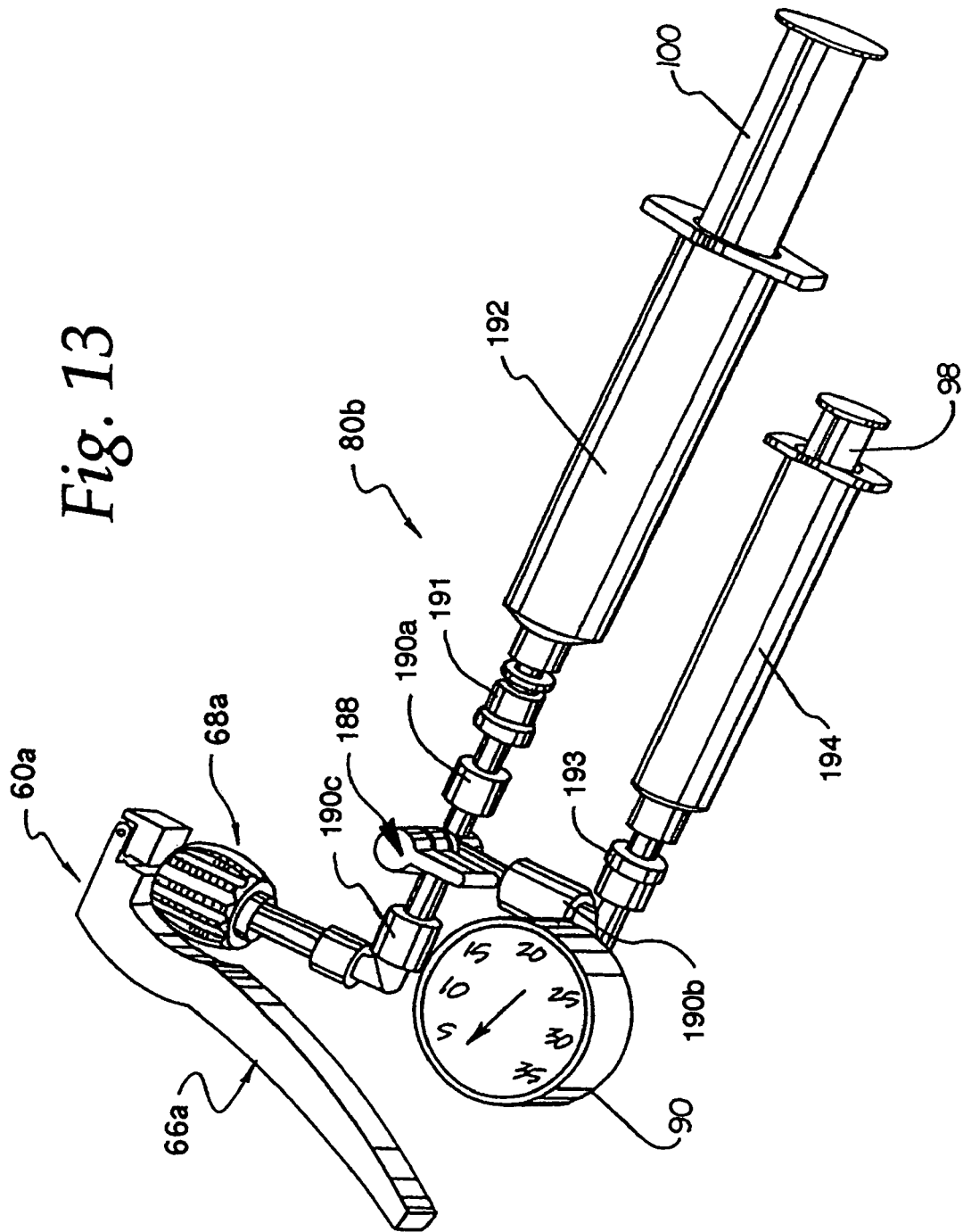

FIG. 13 shows an alternative gas inflation/evacuation system 80b in use with sealing system 60a. Valve arrangement 188 has three interconnect fittings 190a, 190b and 190c. Attached to interconnect fitting 190a is evacuation syringe 192. Evacuation syringe 192 includes evacuation syringe plunger 100. Attached to interconnect fitting 190b is pressure gauge 90. Pressure gauge 90 is fluidly interconnected to inflation syringe 194. Inflation syringe 194 includes inflation syringe plunger 98. Attached to the interconnect fitting 190c is sealing system 60a comprised of crimping mechanism 66a and sealing mechanism 68a. Preferably, one-way check valves 191 and 193 are respectively connected between interconnect fitting 190a and evacuation syringe 192 and between interconnect fitting 190b and inflation syringe 194 as a safety measure to ensure only one-way flow of the gas within the gas inflation/evacuation system 80b. One-way check valve 193 ensures that only the carbon dioxide gas is delivered out of the gas inflation/evacuation system and prevents any reinfusion of air that has been evacuated from the gas inflation/evacuation system.

Figure 14:
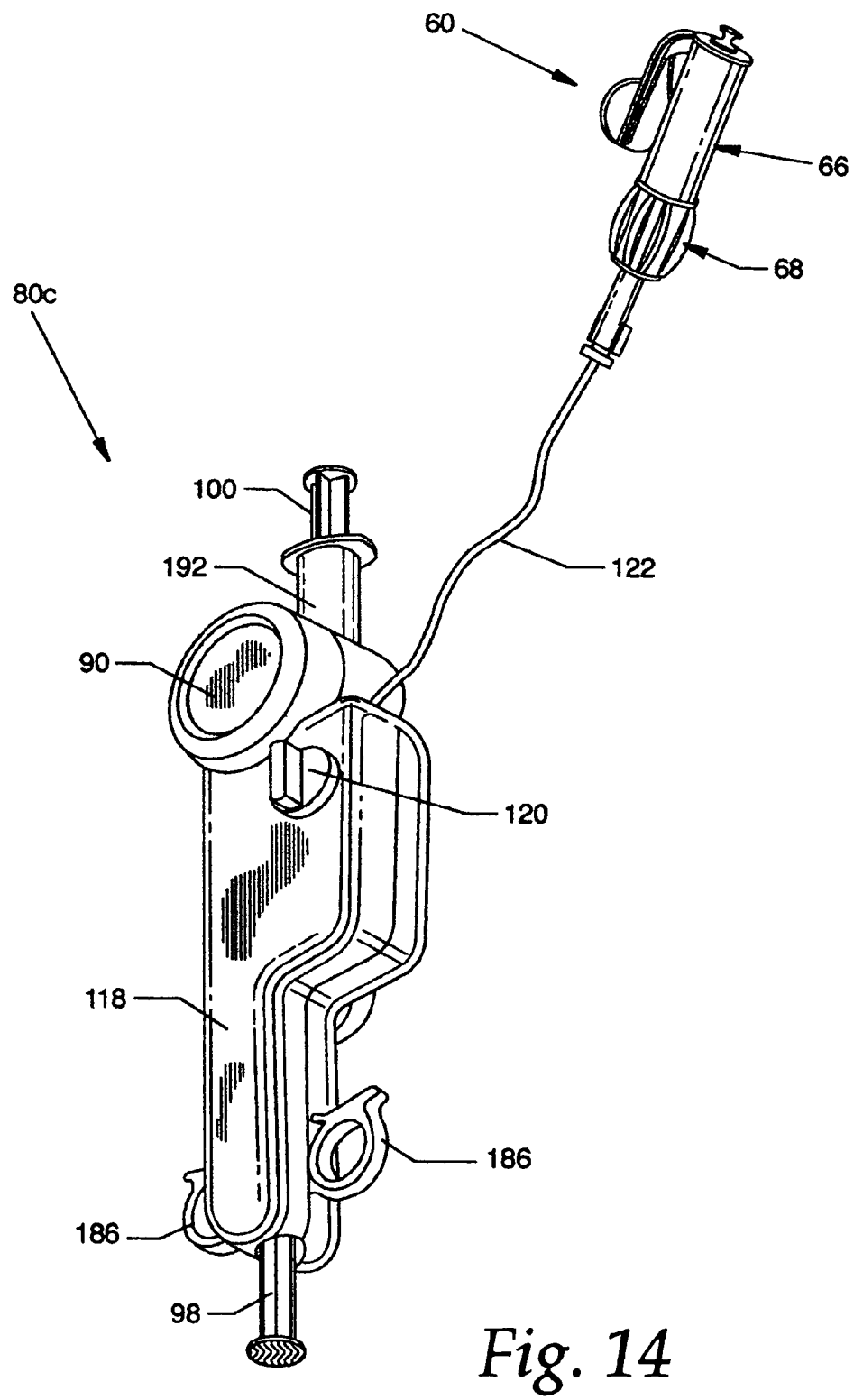
Figure 15:
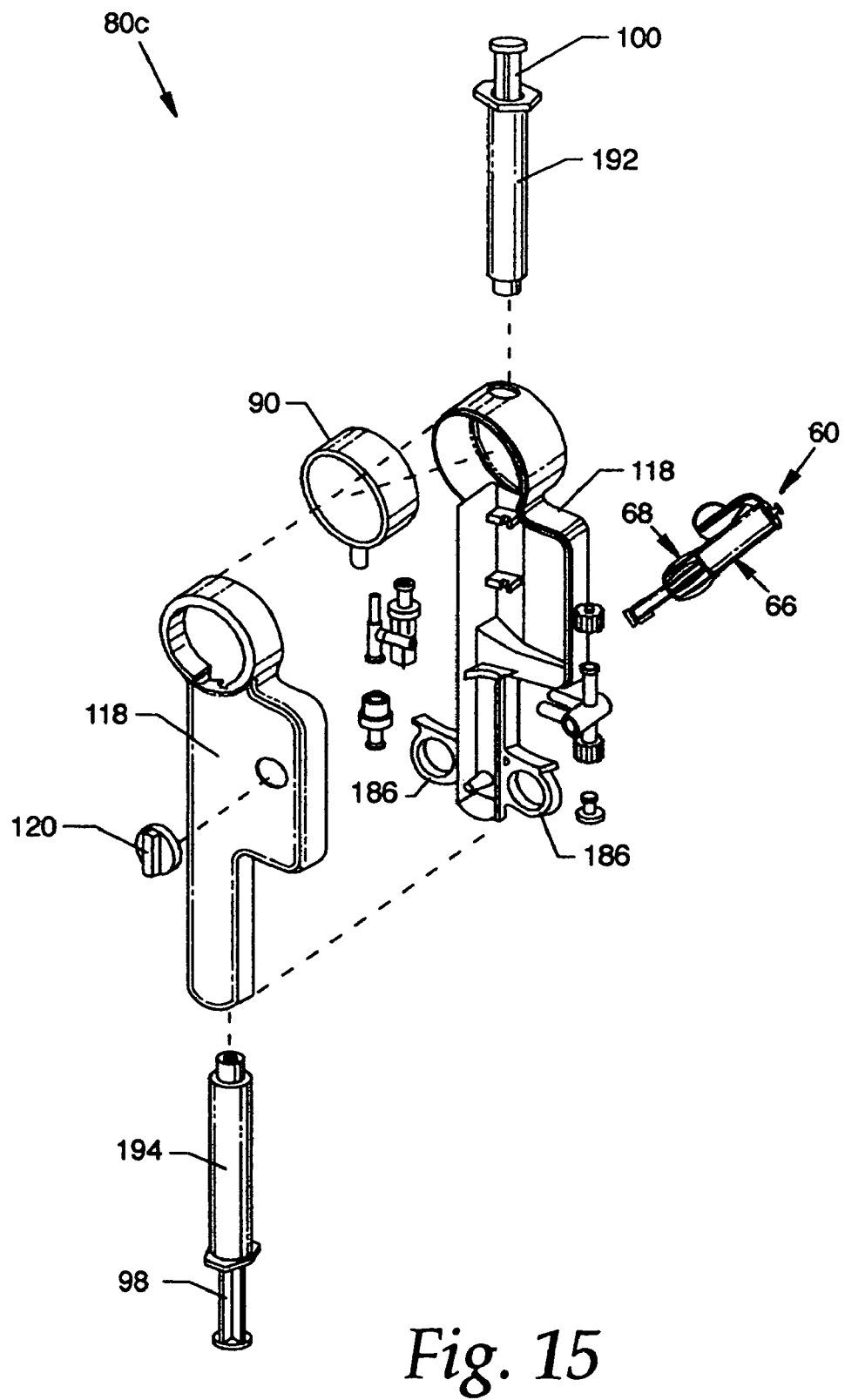
FIG. 15 is an exploded view of the gas inflation/evacuation system of the alternate embodiment shown in FIG. 14 and the associated sealing system.

FIGS. 14 and 15 show an alternative gas inflation/evacuation system 80c with sealing system 60. Assembly body 118 contains inflation syringe 194 and evacuation syringe 192. Inflation syringe 194 includes inflation syringe plunger 98. Evacuation syringe 192 includes evacuation syringe plunger 100. Knob 120 connected to valve arrangement 188 is mounted on the exterior of assembly body 118. Pressure gauge 90 is contained within assembly body 118. Assembly body 118 contains fingergrips 186. Conduit 122 is attached to assembly body 118. At the distal end of conduit 122 is sealing system 60 which is comprised of crimping mechanism 66 and sealing mechanism 68.

Figure 16:
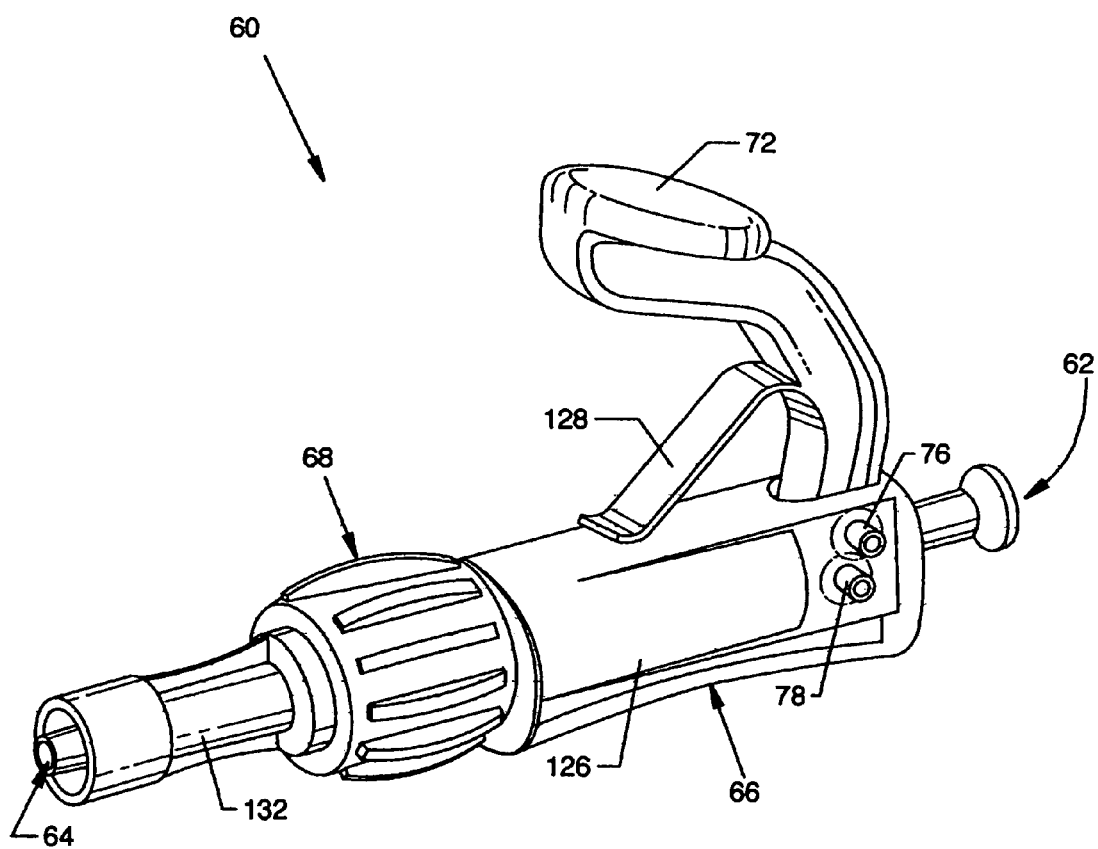
FIG. 16 is a perspective view of the sealing system illustrated with the alternate embodiment shown in FIG. 14.

FIG. 16 shows an embodiment of the sealing system. Specifically, FIG. 16 shows sealing system 60 which is comprised of sealing mechanism 68 and crimping mechanism 66. Crimping mechanism 66 is comprised of crimp body 126, handle 72, handle return 128, and first aperture 62. Sealing mechanism 68 is comprised of sealing body 132 and second aperture 64. Sealing system 60 has a passageway 70 (see FIGS. 8 and 9) fluidly interconnecting first aperture 62 and second aperture 64.

Figure 17:
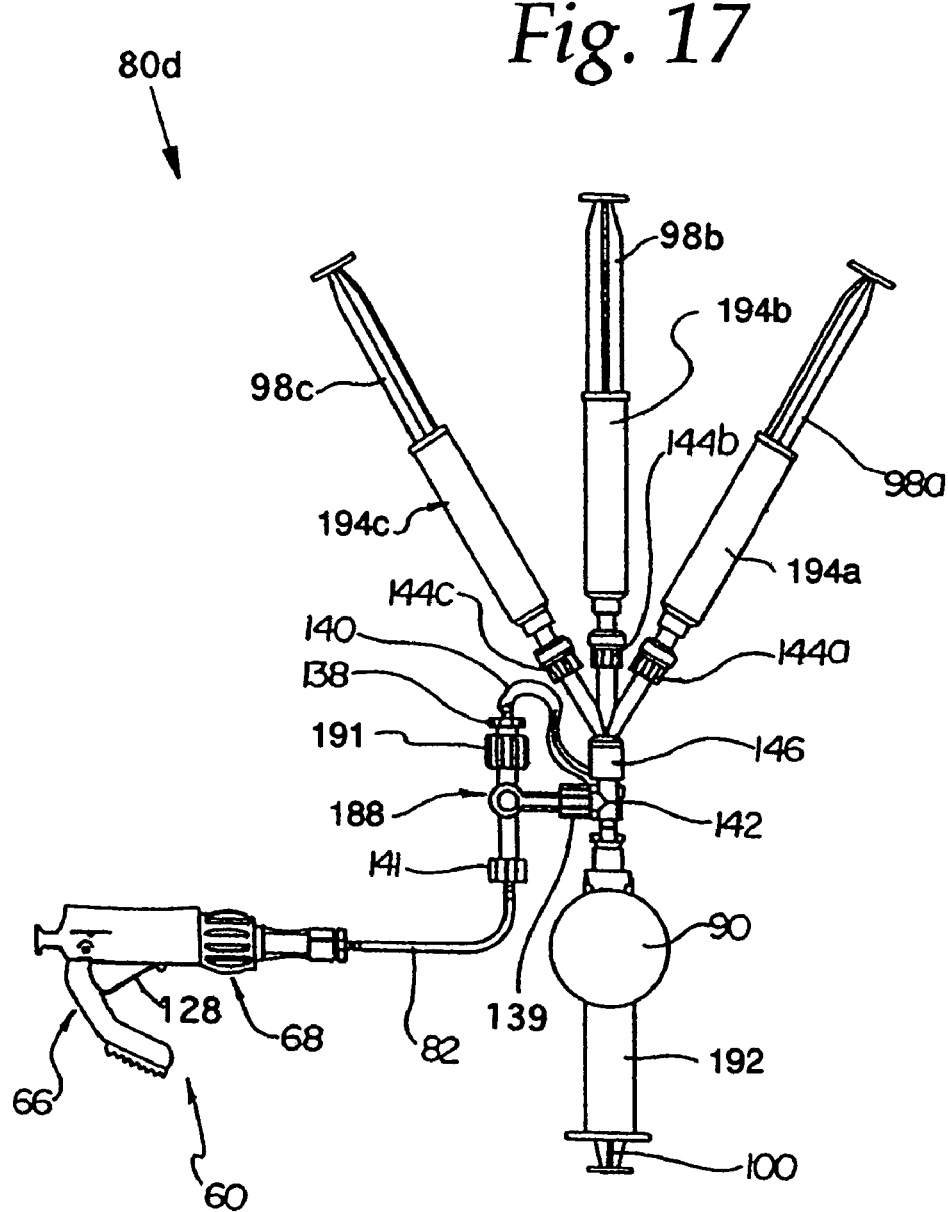
FIG. 17 is a top view of a preferred embodiment of a gas inflation/evacuation system and sealing system of the present invention.

FIG. 17 shows an alternative gas inflation/evacuation assembly 80d coupled to sealing system 60. Valve arrangement 188 has a coupling 141 connected to conduit 82 and a port 138 that is attached via one-way check valve 191 and hose 140 to evacuation syringe 192. Attached to an interconnect fitting 139 of the valve arrangement 188 is inflation manifold 142. Inflation manifold 142 is connected to connector 146 and pressure gauge 90. Inflation manifold 142 has three check valves 144a, 144b and 144c. Check valves 144a, 144b and 144c are connected to respective inflation syringes 194a, 194b and 194c which have respective inflation syringe plungers 98a, 98b, and 98c. In this embodiment, evacuation syringe 192 is mounted behind pressure gauge 90. As with the other embodiments, the distal end of conduit 82 is connected to sealing system 60. Sealing system 60 is comprised of sealing mechanism 68 and crimping mechanism 66.

Figure 18:
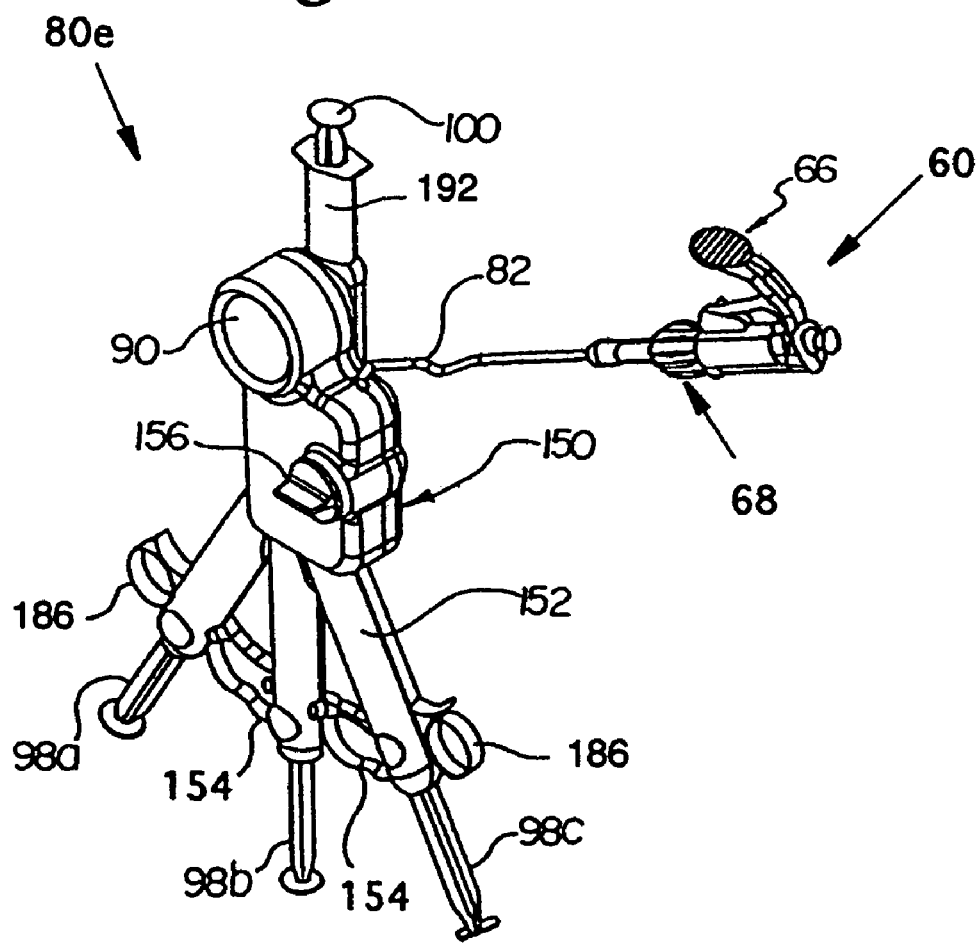
FIG. 18 is a perspective view of another alternate embodiment of a gas inflation/evacuation system and sealing system.

FIG. 18 shows an alternative gas inflation/evacuation system 80e that is similar to the gas inflation/evacuation system 80d shown in FIG. 17 except that the components are arranged in a common housing 150. Common housing 150 has internal sealed channels that fluidly interconnect via valve arrangement 188 to evacuation syringe 192 and to inflation syringes 194a, 194b and 194c and pressure gauge 90. Common housing 150 has structure 152 that defines chambers for the three inflation syringes 194a, 194b and 194c. Common housing 150 also includes structure defining external fingergrips 186 and internal fingergrips 154 between adjacent portions of structure 152. Common housing 150 also contains structure for integrating evacuation syringe 192 and pressure gauge 90 as part of the common housing 150. An external knob 156 connects to the valve arrangement 188.

Figure 25:
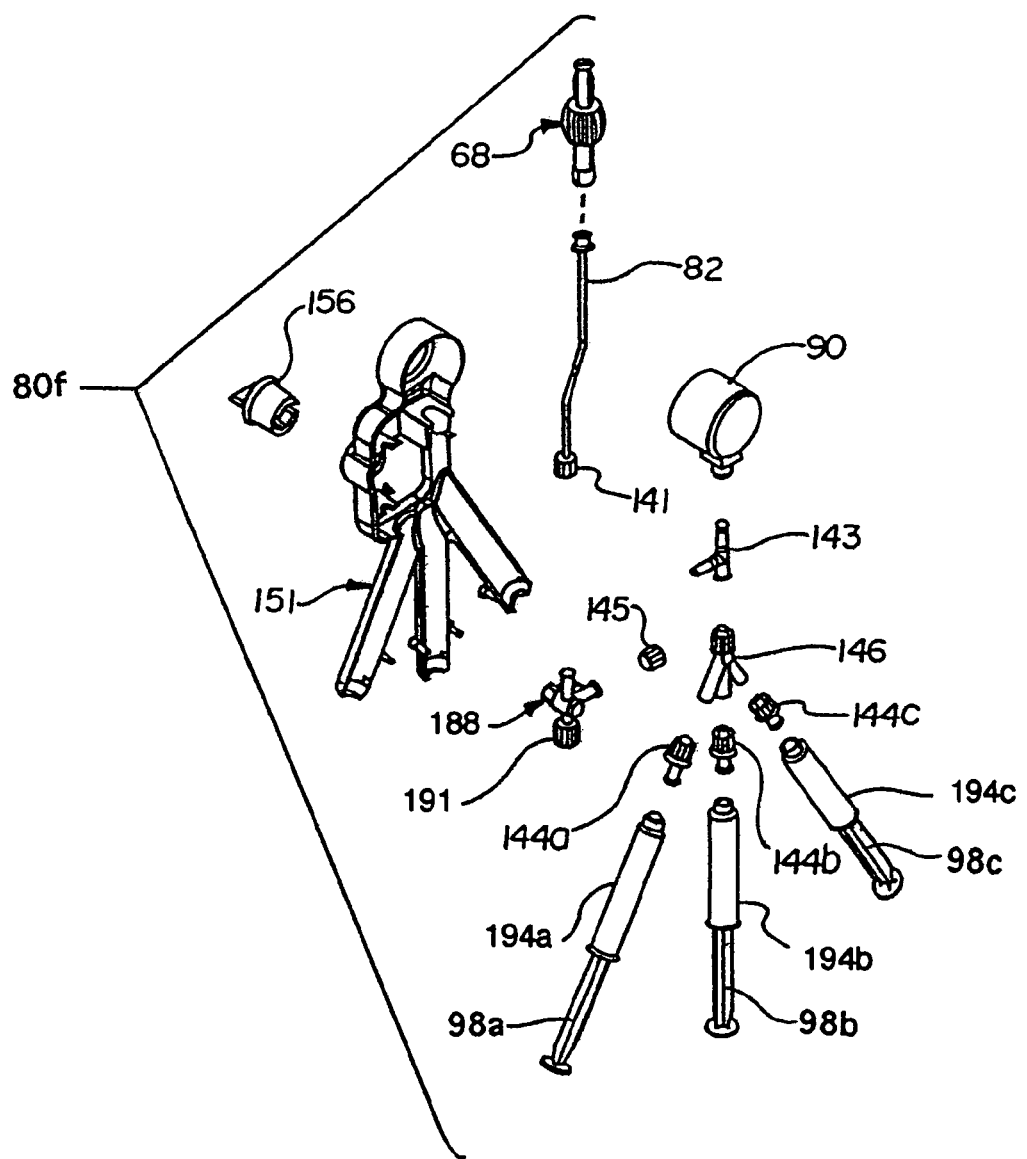
FIG. 25 is an exploded view of still another alternate embodiment of a gas inflation/evacuation system and sealing system; and, FIG. 26 is a partially exploded view of the alternate embodiment of FIG. 18 including the entire joinable housing assembly thereof.
Figure 26:
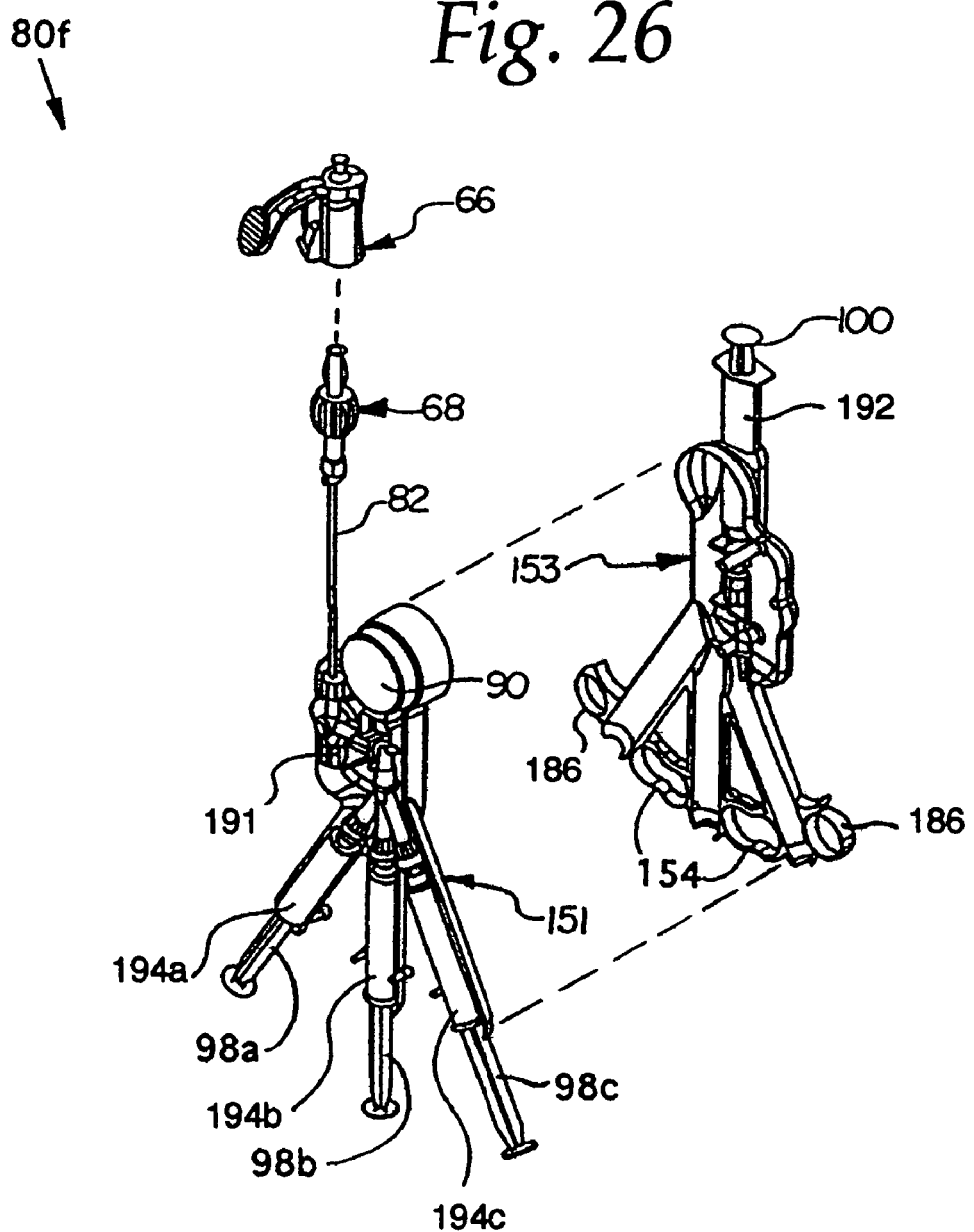

FIGS. 25 and 26 show an alternative embodiment to that shown in FIG. 18. Rather than utilizing the common housing 150 with internal sealed channels, an assembled gas inflation/evacuation system 80f, substantially similar to the gas inflation/evacuation system 80d shown in FIG. 17, is securely placed within a two-part housing such that the two-part housing provides a protective and functional casing around the gas inflation/evacuation system 80f. As demonstrated in the exploded view of FIG. 25, the previously described components of the gas inflation/evacuation system 80d are assembled prior to fitting of the housing. In addition to the components described above with relation to FIG. 17, this exploded view shows two additional components: namely, tee connector 143 and coupling 145. Tee connector 143 is intermediately connected to pressure gauge 90 at one end and connector 146 at the other end. Further, coupling 145 interconnects valve arrangement 188 to tee connector 143. Upon completion of the component assembly, the assembled system is securely placed within a top housing half 151, as shown in FIG. 26. Once secured, a compatible bottom housing half 153, as also shown in FIG. 26, is joined with top housing half 151 to form the full housing. This joining of top housing half 151 and bottom housing half 153 can be achieved using a myriad of techniques, such as adhesive bonding, heat bonding, chemical bonding, pressure fittings, snap connectors, clip connectors, fasteners such as screws and bolts, and the like.

The embodiments shown in FIGS. 17, 18, 25 and 26 allow for effective pressurization of occlusive balloon 32 at less than 2 atmospheres while reducing the total volume of gas that might be introduced into a patient in the event of a leak in the guidewire occlusion system 20. Depending upon the desired inflation pressure and the total number of inflation cycles, the total amount of pressurized gas in a single inflation syringe such as 88 in FIGS. 8 and 9 or 194 in FIGS. 12-15 can be significant. If a leak were to occur, the entire contents of a single inflation syringe would be susceptible to that leak. By using a separate inflation syringe 194a, 194b, 194c for each inflation in the embodiments shown in FIGS. 17, 18, 25 and 26, these alternate embodiments provide a simple way of decreasing the total amount of pressurized gas that might be introduced into a patient in the event of a leakage in the guidewire occlusion system 20.

A similar result could be achieved by manually attaching separate inflation syringes 194a, 194b, 194c and an evacuation syringe 192 directly to the sealing system 60 by way of a Luer lock or the like. While such an embodiment would not be as quick or convenient as the preferred embodiment, this alternative would eliminate the volume of gas required for the conduit 82 and within common housing 150, as well as the need for a valve arrangement 188.

Figure 22:
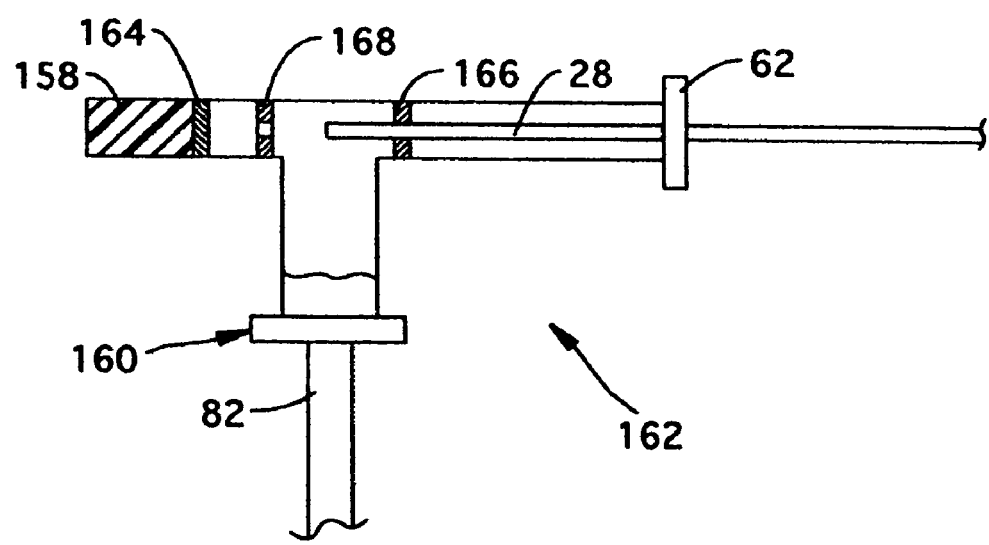
FIG. 22 is a cross sectional view of an alternate embodiment of a sealing system showing one embodiment of a plugging mechanism.

In alternate embodiments, the sealing system could include means for selectively sealing involving techniques other than crimping to accomplish multiple airtight seals along the course of the extended sealable section 28. One alternate embodiment, as portrayed in FIG. 22, would involve the insertion of some form of sealant material 158 into the proximal end of the extended sealable section 28, such as wax, plastic, polymer or metal inserts or plugs. Conduit 82 is attached to a plugging mechanism 162 through the conduit aperture 160. In this embodiment, sealant material 158 is confined by sealant confinement layer 164 residing within plugging mechanism 162. Preferably for this embodiment, sealant material 158 is a wax or gel that is flowable at higher temperatures and might be melted during sterilization of the sealing system. Sealant confinement layer 164 is a foil layer or thin layer of non-meltable material capable of confining a flowable material during any sterilization process or exposure to higher temperature. The proximal end of extended sealable section 28 is inserted through first aperture 62 until it is past operational O-ring 166 or some other form of sealable/deformable material such as a silicone puncture seal or similar membrane seal. When it is desired to seal the extended sealable section 28, the extended sealable section 28 is further inserted past a sealant O-ring 168, then through sealant confinement layer 164, and finally into sealant material 158. Sealant material 158 is deposited in the proximal end of extended sealable section 28, thus preventing the guidewire assembly 22 from being evacuated. Extended sealable section 28 can then be slidably withdrawn through the sealant O-ring 168, through the operational O-ring 166, and through the first aperture 62, thereby effectively disengaging the guidewire assembly 22 from the plugging mechanism 162. The O-rings 166 and 168 serve as wiping structures to remove excess sealant material from the outside of the extended sealable section 28. Other alternate embodiments involve heating the extended sealable section 28 when it is formed of metal or polymer material so as to create a constriction, or applying electrical or magnetic energy to arc or weld material within the extended sealable section 28 to create a constriction. In one embodiment, the equivalent of a spot welder could be used in place of the crimping mechanism 66 to accomplish the same purpose of sealing, and then severing the extended sealable section 28. Alternative embodiments could use other sealing techniques to seal the guidewire assembly 22. These methods could include, but are not limited to, ones utilizing a heat source to melt the extended sealable section, ones using a heat source to apply a glue or gel, methods involving insertion of a plug material, methods using magnetics to manipulate a sealing material, or methods utilizing small occlusive devices.

Depending on the sealing method specified in an embodiment, different deflation techniques can be utilized. For the preferred embodiment, the extended sealable section 28 is of sufficient length to allow deflation through the shearing, breaking or opening of the extended sealable section 28 distal to the sealant material 158 located in the proximal end of the extended sealable section 28. By having sufficient length of the extended sealable section 28, the guidewire assembly 22 can be coupled to the gas inflation/evacuation system 80 (or 80a-80f) multiple times, allowing the occlusive balloon 32 to be inflated and deflated multiple times. Other embodiments will use methods of deflation including melting the sealant material 158, removing a plug of sealant material 158, and various other methods not requiring the extended sealable section 28 to be sheared.

Figure 23:
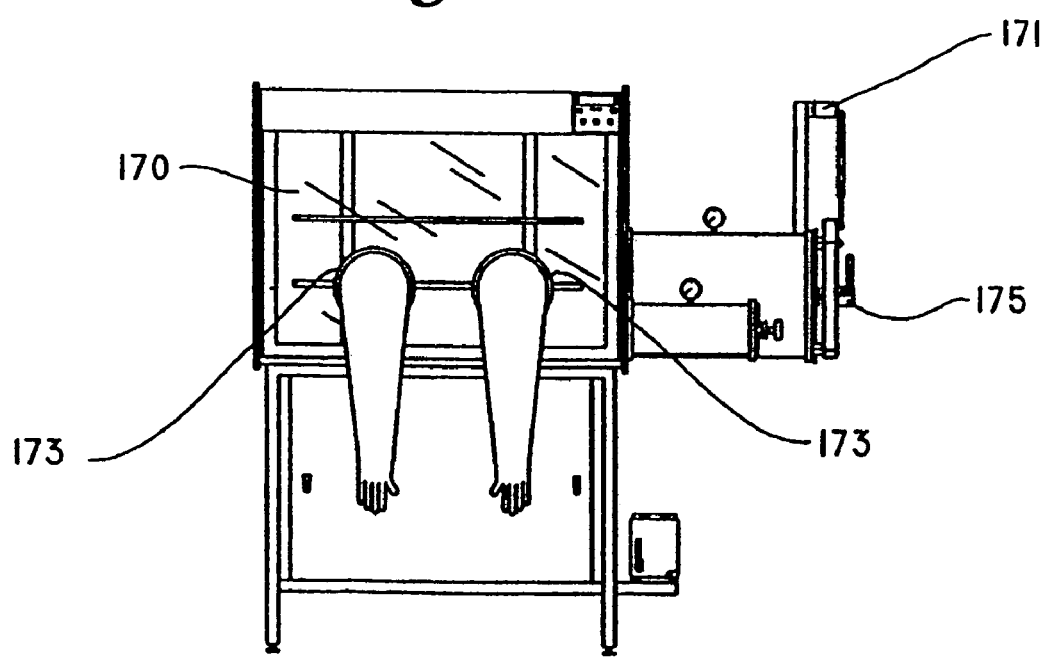
FIG. 23 is a schematic view of equipment including a sealed chamber for use in assembling and packaging the guidewire occlusion system.

In one embodiment, the guidewire occlusion system 20 is preferably pre-assembled and packaged in an environment consisting of an appropriate biocompatible gas. FIG. 23 shows equipment with which the guidewire occlusion system 20 is assembled and packaged. The guidewire occlusion system 20 is assembled and packaged in a sealed chamber 170. Sealed chamber 170 is equipped with a venting duct 171, sealed handling ports 173, and an atmosphere control system 175. The venting duct 171 and atmosphere control system 175 provide the overall system for maintaining a biocompatible gas atmosphere within the sealed chamber 170. Sensory readings within the sealed chamber 170 provide the atmosphere control system 175 with the data needed to adjust the biocompatible gas levels within the sealed chamber 170. Stored biocompatible gas is introduced into the sealed chamber 170 through the venting duct 171. Assembling and packaging of the guidewire occlusion system 20 and/or any of the pre-assembled components is achieved with the use of the sealed handling ports 173. The ports 173 are sterilized and sealed so that an assembler or packager positioned outside the sealed chamber 170 can access the contents of the chamber without introducing contamination through actual human contact or through the introduction of undesirable gases and airborne contaminants. These ports 173 could be constructed of flexible glove-like attachments, as shown, or they could be robotic devices operable within the sealed chamber 170 through controls external to the sealed chamber 170. The equipment could be two or more sealed chambers.

Figure 24:
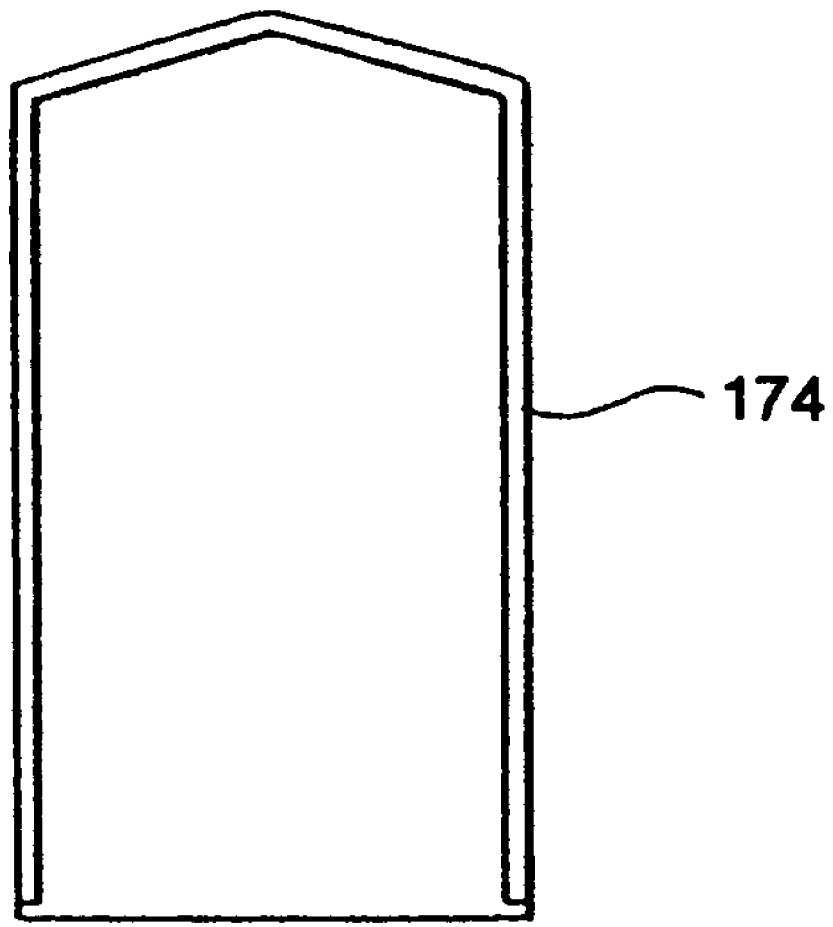
FIG. 24 is a side view of a biocompatible packaging.

After a guidewire assembly 22, a sealing system 60 (or 60a) and a gas inflation/evacuation system 80 (or 80a-80f) are placed in a sealed chamber 170, they are assembled to form the guidewire occlusion system 20 and placed into biocompatible packaging 174 (FIG. 24). Biocompatible packaging 174 is hermetically sealed so that the internal volume of both biocompatible packaging 174 and guidewire occlusion system 20 is composed solely of biocompatible gas. A preferred embodiment of the biocompatible packaging 174 is shown in FIG. 24. The biocompatible packaging 174 is preferably in the form of a foil pouch. This foil pouch is made from a medical packaging film with the following laminates: an 8.75 micron foil layer, an adhesive layer, a white polyethylene layer, and a 12 micron PET layer. The foil pouch has a preferred total thickness of approximately 3.6 millimeters, and a minimum bond strength of one pound. In addition, the preferred barrier properties of the film will be an oxygen transmission <0.01 cc/100 sq. in/24 hr. (73 degrees F., 0% RH) ASTM 3985, and moisture vapor transmission <0.01 gm H2O/100 sq. in/24 hr. (100 degrees F., 90% RH) ASTM F1249. It will be understood by those skilled in the art that this biocompatible foil pouch can be contained and/or attached within an outer packaging or container, such as a cardboard box, a plastic container, or the like. Such an outer packaging will facilitate shipping, labeling, storage, and handling of the biocompatible packaging 174 and its contents.

In practice, medical personnel gain access to the vessel lumen through which the guidewire assembly 22 will travel. The guidewire occlusion system 20 is removed from biocompatible packaging 174. Flexible tip 38 is inserted in the vessel lumen and is manipulated to a point beyond the vessel occlusion. Valve arrangement 84 (or 188) is adjusted to the evacuation position and evacuation syringe plunger 92 (or 100) is slidably withdrawn to remove any gas present in the guidewire assembly 22. Valve arrangement 84 (or 188) is then adjusted to the inflation position and inflation syringe plunger 94 (or 98, 98a, 98b, 98c) is slidably inserted causing occlusive balloon 32 to inflate.

Following inflation of occlusive balloon 32, handle 72 of the crimping mechanism 66 (or the handle of 66a) is depressed causing roller 76 and roller 78 to crimp and preferably sever the extended sealable section 28 of guidewire assembly 22. Severing of the extended sealable section 28 serves as an immediate verification of the creation of an effective seal. Sealing mechanism 68 (or 68a) can be released and guidewire assembly 22 can be completely removed from the sealing system 60 (or 60a) allowing the occlusive balloon 32 to remain inflated while occlusive substance treatment occurs. Following treatment, the extended sealable section 28 can be sheared or broken off, resulting in the deflation of the occlusive balloon 32. If occlusive treatment is complete, guidewire assembly 22 can be removed from the vessel lumen. If additional treatment is required, extended sealable section 28 can be reattached to sealing system 60 (or 60a) through first aperture 62. Sealing mechanism 68 (or 68a) can be retightened and the evacuation/inflation process can be repeated.

In a preferred embodiment of the present invention, the guidewire assembly 22 is utilized as the guidewire for an atherectomy or thrombectomy procedure of the type described in U.S. Pat. Nos. 5,370,609 or 5,496,267, the disclosures of both of which are hereby incorporated by reference. In each of these procedures, the guidewire assembly 22 is introduced into the patient, the occlusive balloon 32 is inflated, and then the atherectomy or thrombectomy catheter arrangement is slid over the proximal end 36 of the guidewire assembly 22 and advanced until it is proximate and proximal to the location of the occlusive balloon. The procedure is performed for a time period consistent with the desired maximum length for blockage of the particular vessel at which time the extended sealable section 28 of the guidewire assembly 22 may be severed to deflate the occlusive balloon 32, thereby reestablishing blood flow within the vessel. Depending upon the nature of the procedure, the catheter arrangement may be removed from the vessel or left in place. Preferably, an evacuation of any plaque material or other debris dislodged by the therapy is accomplished before deflation of the occlusive balloon 32. The occlusive balloon 32 is reinflated prior to reinitiation of the procedure.

The present invention may be embodied in other specific forms without departing from the essential attributes thereof; therefore, the illustrated embodiments should be considered in all respects as illustrative and not restrictive, reference being made to the appended claims rather than to the foregoing description to indicate the scope of the invention.

Various modifications can be made to the present invention without departing from the apparent scope thereof.

The invention claimed is:

1. A storable gas inflation/evacuation system and sealing system removably connectible to a proximal portion of a guidewire assembly which has an occlusive balloon at a distal portion thereof, including provision for indicating the presence of oxygen, comprising:
   a sealable container that isolates contents of the sealable container from ambient atmosphere when sealed;
   an oxygen-sensitive material located within the sealable container, the oxygen-sensitive material being inactive prior to exposure to radiation and activatable by exposure to radiation, the activation of the oxygen-sensitive material causing the oxygen-sensitive material to become sensitive to oxygen exposure only after activation and to remain sensitive to oxygen exposure after completion of radiation exposure and to undergo a visual change in response to such post-radiation oxygen exposure;
   means for evacuating the guidewire assembly;
   means for introducing a biocompatible gas into the guidewire assembly to inflate the occlusive balloon at the distal portion of the guidewire assembly a plurality of times;
   means for selectively sealing the guidewire assembly by forming successive permanent airtight seals at separate locations along the proximal portion of the guidewire assembly to retain the biocozupatible gas in the occlusive balloon a plurality of times, the means for selectively sealing including a mechanism selected from the group of mechanisms consisting of a crimping mechanism and a plugging mechanisn; and,
   wherein the oxygen-sensitive material is separate from the means for evacuating, the means for introducing, and the means for selectively sealing.

2. The storable gas inflation/evacuation system and sealing system of claim 1, wherein the means for evacuating, the means for introducing a biocompatible gas, and the means for selectively sealing constitute a handheld apparatus.

3. The storable gas inflation/evacuation system and sealing system of claim 1, wherein the mechanism is a crimping mechanism.

4. The storable gas inflation/evacuation system and sealing system of claim 1, wherein the means for evacuating, the means for introducing a biocompatible gas, and the means for selectively sealing are contained in a sterile packaging filled with a biocompatible gas and wherein all gas within the sterile packaging is selected from the group consisting of carbon dioxide, oxygen, and nitrous oxide.

5. A storable gas inflation/evacuation system and sealing system removably connectible to a proximal portion of a guidewire assembly which has an occlusive balloon at a distal portion thereof, including provision for indicating the presence of oxygen, comprising:
   a sealable container that isolates contents of the sealable container from ambient atmosphere when sealed;
   an oxygen-sensitive material located within the sealable container, the oxygen-sensitive material being inactive prior to exposure to radiation and activatable by exposure to radiation, the activation of the oxygen-sensitive material causing the oxygen-sensitive material to become sensitive to oxygen exposure only after activation and to remain sensitive to oxygen exposure after completion of radiation exposure and to undergo a visual change in response to such post-radiation oxygen exposure;
   a first syringe that selectively evacuates the guidewire assembly;
   a second syringe that selectively introduces a biocompatible gas into the guidewire assembly to inflate the occlusive balloon at the distal portion of the guidewire assembly a plurality of times;
   a sealing assembly removably connectible to the proximal portion of the guidewire assembly, the sealing assembly including a mechanism that selectively seals the proximal portion of the guidewire assembly at one of a plurality of separate locations to form one of a plurality of successive permanent airtight seals of the guidewire assembly;
   a valve arrangement that selectively opens and closes communication between the sealing assembly and the first syringe and between the sealing assembly and the second syringes; and
   wherein the oxygen-sensitive material is separate from the first syringe, the second syringe, the sealing assembly, and the valve arrangement.

6. A storable gas inflation/evacuation system and sealing system selectively operably connectible to and removable from a proximal portion of a guidewire assembly which has an occlusive balloon at a distal portion thereof, including provision for indicating the presence of oxygen, comprising:
   a sealable container that isolates contents of the sealable container from ambient atmosphere when sealed;
   an oxygen-sensitive material located within the sealable container, the oxygen-sensitive material being inactive prior to exposure to radiation and activatable by exposure to radiation, the activation of the oxygen-sensitive material causing the oxygen-sensitive material to become sensitive to oxygen exposure only after activation and to remain sensitive to oxygen exposure after completion of radiation exposure and to undergo a visual change in response to such post-radiation oxygen exposure;

a handheld unit including a crimping mechanism having a first aperture and a sealing mechanism having a second aperture, there being a passageway extending from the first aperture to the second aperture for receiving the proximal portion of the guidewire assembly;

a first syringe system that selectively evacuates the guidewire assembly;

a second syringe system containing a volume of a biocompatible gas sufficient to inflate the occlusive balloon at the distal portion of the guidewire assembly a plurality of times;

conduits operably connecting the first syringe system and the second syringe system to the second aperture of the handheld unit, the conduits including a valve arrangement that selectively connects only one of the first syringe system and the second syringe system to the second aperture at a time;

wherein the oxygen-sensitive material is separate from the handheld unit, the first syringe system, the second syringe system, and the conduits.

7. A storable gas inflation/evacuation system and sealing system removably connectible to a proximal portion of a guidewire assembly which has an occlusive balloon at a distal portion thereof, including provision for indicating the presence of oxygen, comprising:

a sealable container that isolates contents of the sealable container from ambient atmosphere when sealed;

an oxygen-sensitive material located within the sealable container, the oxygen-sensitive material being inactive prior to exposure to radiation and activatable by exposure to radiation, the activation of the oxygen-sensitive material causing the oxygen-sensitive material to become sensitive to oxygen exposure only after activation and to remain sensitive to oxygen exposure after completion of radiation exposure and to undergo a visual change in response to such post-radiation oxygen exposure;

a handheld unit including a crimping mechanism having a first aperture and a sealing mechanism having a second aperture, there being a passageway extending from the first aperture to the second aperture for receiving the proximal portion of the guidewire assembly;

an evacuating syringe that selectively evacuates the guidewire assembly;

a plurality of inflation syringes, each inflation syringe containing a volume of a biocompatible gas sufficient to inflate the occlusive balloon at the distal portion of the guidewire assembly a single time; and wherein the oxygen-sensitive material is separate from the handheld unit, the evacuating syringe, and the plurality of inflation syringes.

8. A storable gas inflation/evacuation system and sealing system removably connectible to a proximal portion of a guidewire assembly which has an occlusive balloon at a distal portion thereof, including provision for indicating the presence of oxygen, comprising:

a sealable container that isolates contents of the sealable container from ambient atmosphere when sealed;

an oxygen-sensitive material located within the sealable container, the oxygen-sensitive material being inactive prior to exposure to radiation and activatable by exposure to radiation, the activation of the oxygen-sensitive material causing the oxygen-sensitive material to become sensitive to oxygen exposure only after activation and to remain sensitive to oxygen exposure after completion of radiation exposure and to undergo a visual change in response to such post-radiation oxygen exposure;

a first syringe system that selectively evacuates the guidewire assembly;

a second syringe, system that selectively introduces a biocompatible gas into the guidewire assembly to inflate the occlusive balloon at the distal portion of the guidewire assembly a plurality of times;

a plugging mechanism removably connectible to the proximal portion of the guidewire assembly that selectively seals the proximal portion of the guidewire assembly at one of a plurality of separate locations to form one of a plurality of successive permanent airtight seals of the guidewire assembly, including:

a first aperture and a second aperture in fluid communication, the first aperture being capable of receiving therethrough the proximal portion of the guidewire assembly, and the second aperture being removably attachable to a conduit;

an operational O-ring in coaxial alignment with the first aperture f or operational engagement of the proximal portion of the guidewire assembly at a location proximal of the first aperture;

a sealant O-ring in coaxial alignment with the first aperture and proximally spaced from the operational O-ring such that further insertion of the proximal portion of the guidewire assembly through the first aperture and past the operational O-ring will bring the proximal portion of the guidewire assembly into engagement with the sealant O-ring; and, a sealant confinement layer for receiving the proximal portion of the guidewire assembly some distance past the sealant O-ring, the sealant confinement layer confining sealant material such that insertion of the proximal portion of the guidewire assembly through the sealant confinement layer and into the sealant material forces the sealant material into the proximal portion of the guidewire assembly; and wherein the oxygen-sensitive material is separate from the first syringe system, the second syringe system, and the plugging mechanism.

9. A storable gas inflation/evacuation system and sealing system removably connectible to a proximal portion of a guidewire assembly which has an occlusive balloon at a distal portion thereof, including provision f or indicating the presence of oxygen, comprising:

a sealable container that isolates contents of the sealable container from ambient atmosphere when sealed;

an oxygen-sensitive material located within the sealable container, the oxygen-sensitive material being inactive prior to exposure to radiation and activatable by exposure to radiation, the activation of the oxygen-sensitive material causing the oxygen-sensitive material to become sensitive to oxygen exposure only after activation and to remain sensitive to oxygen exposure after completion of radiation exposure and to undergo a visual change in response to such post-radiation oxygen exposure;

means for evacuating the guidewire assembly;

means for introducing a biocompatible gas into the guidewire assembly to inflate the occlusive balloon at the distal portion of the guidewire assembly a plurality of times;

means for selectively sealing the guidewire assembly by forming successive permanent airtight seals at separate locations along the proximal portion of the guidewire assembly to retain the biocoxupatible gas in the occlusive balloon a plurality of times, the means for selectively sealing including a mechanism selected from the group of mechanisms consisting of a crimping mechanism and a plugging mechanism; and, wherein the oxygen-sensitive material is present in at least one of the the means for evacuating, the means for introducing, and the means for selectively sealing.

10. The storable gas inflation/evacuation system and sealing system of claim 9, wherein the means for evacuating, the means for introducing a biocompatible gas, and the means for selectively sealing constitute a handheld apparatus.

11. The storable gas inflation/evacuation system and sealing system of claim 9, wherein the mechanism is a crimping mechanism.

12. The storable gas inflation/evacuation system and sealing system of claim 9, wherein the means for evacuating, the means for introducing a biocompatible gas, and the means for selectively sealing are contained in a sterile packaging filled with a biocompatible gas and wherein all gas within the sterile packaging is selected from the group consisting of carbon dioxide, oxygen, and nitrous oxide.

13. A storable gas inflation/evacuation system and sealing system removably connectible to a proximal portion of a guidewire assembly which has an occlusive balloon at a distal portion thereof, including provision for indicating the presence of oxygen, comprising;
a sealable container that isolates contents of the sealable container from ambient atmosphere when sealed;
an oxygen-sensitive material located within the sealable container, the oxygen-sensitive material being inactive prior to exposure to radiation and activatable by exposure to radiation, the activation of the oxygen-sensitive material causing the oxygen-sensitive material to become sensitive to oxygen exposure only after activation and to remain sensitive to oxygen exposure after completion of radiation exposure and to undergo a visual change in response to such post-radiation oxygen exposure;
a first syringe that selectively evacuates the guidewire assembly;
a second syringe that selectively introduces a biocompatible gas into the guidewire assembly to inflate the occlusive balloon at the distal portion of the guidewire assembly a plurality of times;
a sealing assembly removably connectible to the proximal portion of the guidewire assembly, the sealing assembly including a mechanism that selectively seals the proximal portion of the guidewire assembly at one of a plurality of separate locations to form one of a plurality of successive permanent airtight seals of the guidewire assembly;
a valve arrangement that selectively opens and closes communication between the sealing assembly and the first syringe and between the sealing assembly and the second syringe; and,
wherein the oxygen-sensitive material is present in at least one of the first syringe, the second syringe, the sealing assembly, and the valve arrangement.

14. A storable gas inflation/evacuation system and sealing system selectively operably connectible to and removable from a proximal portion of a guidewire assembly which has an occlusive balloon at a distal portion thereof, including provision for indicating the presence of oxygen, comprising:
a sealable container that isolates contents of the sealable container from ambient atmosphere when sealed;
an oxygen-sensitive material located within the sealable container, the oxygen-sensitive material being inactive prior to exposure to radiation and activatable by exposure to radiation, the activation of the oxygen-sensitive material causing the oxygen-sensitive material to become sensitive to oxygen exposure only after activation and to remain sensitive to oxygen exposure after completion of radiation exposure and to undergo a visual change in response to such post-radiation oxygen exposure;
a handheld unit including a crimping mechanism having a first aperture and a sealing mechanism having a second aperture, there being a passageway extending from the first aperture to the second aperture for receiving the proximal portion of the guidewire assembly;
a first syringe system that selectively evacuates the guidewire assembly;
a second syringe system containing a volume of a biocompatible gas sufficient to inflate the occlusive balloon at the distal portion of the guidewire assembly a plurality of times;
conduits operably connecting the first syringe system and the second syringe system to the second aperture of the handheld unit, the conduits including a valve arrangement that selectively connects only one of the first syringe system and the second syringe system to the second aperture at a time; and,
wherein the oxygen-sensitive material is present in at least one of the handheld unit, the first syringe system, the second syringe system, and the conduits.

15. A storable gas inflation/evacuation system and sealing system removably connectible to a proximal portion of a guidewire assembly which has an occlusive balloon at a distal portion thereof, including provision for indicating the presence of oxygen, comprising:
a sealable container that isolates contents of the scalable container from ambient atmosphere when sealed;
an oxygen-sensitive material located within the sealable container, the oxygen-sensitive material being inactive prior to exposure to radiation and activatable by exposure to radiation, the activation of the oxygen-sensitive material causing the oxygen-sensitive material to become sensitive to oxygen exposure only after activation and to remain sensitive to oxygen exposure after completion of radiation exposure and to undergo a visual change in response to such post-radiation oxygen exposure;
a handheld unit including a crimping mechanism having a first aperture and a sealing mechanism having a second aperture, there being a passageway extending from the first aperture to the second aperture for receiving the proximal portion of the guidewire assembly;
an evacuating syringe that selectively evacuates the guidewire assembly;
a plurality of inflation syringes, each inflation syringe containing a volume of a biocompatible gas sufficient to inflate the occlusive balloon at the distal portion of the guidewire assembly a single time; and,
wherein the oxygen-sensitive material is present in at least one of the handheld unit, the evacuating syringe, and the plurality of inflation syringes.

16. A storable gas inflation/evacuation system and sealing system removably connectible to a proximal portion of a guidewire assembly which has an occlusive balloon at a distal portion thereof, including provision for indicating the presence of oxygen, comprising:
- a sealable container that isolates contents of the sealable container from ambient atmosphere when sealed;
- an oxygen-sensitive material located within the sealable container, the oxygen-sensitive material being inactive prior to exposure to radiation and activatable by exposure to radiation, the activation of the oxygen-sensitive material causing the oxygen-sensitive material to become sensitive to oxygen exposure only after activation and to remain sensitive to oxygen exposure after completion of radiation exposure and to undergo a visual change in response to such post-radiation oxygen exposure;
- a first syringe system that selectively evacuates the guidewire assembly;
- a second syringe system that selectively introduces a biocompatible gas into the guidewire assembly to inflate the occlusive balloon at the distal portion of the guidewire assembly a plurality of times;
- a plugging mechanism removably connectible to the proximal portion of the guidewire assembly that selectively seals the proximal portion of the guidewire assembly at one of a plurality of separate locations to form one of a plurality of successive permanent airtight seals of the guidewire assembly, including:
  - a first aperture and a second aperture in fluid communication, the first aperture being capable of receiving therethrough the proximal portion of the guidewire assembly, and the second aperture being removably attachable to a conduit;
  - an operational O-ring in coaxial alignment with the first aperture for operational engagement of the proximal portion of the guidewire assembly at a location proximal of the first aperture;
  - a sealant O-ring in coaxial alignment with the first aperture and proximally spaced from the operational O-ring such that further insertion of the proximal portion of the guidewire assembly through the first aperture and past the operational O-ring will bring the proximal portion of the guidewire assembly into engagement with the sealant O-ring; and,
  - a sealant confinement layer for receiving the proximal portion of the guidewire assembly some distance past the sealant O-ring, the sealant confinement layer confining sealant material such that insertion of the proximal portion of the guidewire assembly through the sealant confinement layer and into the sealant material forces the sealant material into the proximal portion of the guidewire assembly; and,
- wherein the oxygen-sensitive material is present in at least one of the first syringe system, the second syringe system, and the plugging mechanism.

* * * * *